US008247385B2

(12) United States Patent
Yoo

(10) Patent No.: US 8,247,385 B2
(45) Date of Patent: Aug. 21, 2012

(54) TREATMENT AND PREVENTION OF NEURODEGENERATIVE DISEASES USING GENE THERAPY

(76) Inventor: Tai June Yoo, Memphis, TN (US)

( * ) Notice: Subject to any disclaimer, the term of this patent is extended or adjusted under 35 U.S.C. 154(b) by 320 days.

(21) Appl. No.: 12/025,684

(22) Filed: Feb. 4, 2008

(65) Prior Publication Data

US 2008/0292603 A1 Nov. 27, 2008

Related U.S. Application Data

(60) Provisional application No. 60/900,138, filed on Feb. 6, 2007.

(51) Int. Cl.
*A61K 48/00* (2006.01)
*A01N 63/00* (2006.01)
*A01N 65/00* (2009.01)

(52) U.S. Cl. ............ 514/44 R; 424/93.1; 424/93.2
(58) Field of Classification Search .................. None
See application file for complete search history.

(56) References Cited

U.S. PATENT DOCUMENTS

| | | | |
|---|---|---|---|
| 4,650,764 A | 3/1987 | Temin et al. |
| 5,252,479 A | 10/1993 | Srivastava |
| 5,399,346 A | 3/1995 | Anderson et al. |
| 5,437,994 A | 8/1995 | Emerson et al. |
| 5,580,859 A | 12/1996 | Felgner et al. |
| 5,589,466 A | 12/1996 | Felgner et al. |
| 5,646,043 A | 7/1997 | Emerson et al. |
| 5,670,147 A | 9/1997 | Emerson et al. |
| 5,670,351 A | 9/1997 | Emerson et al. |
| 5,676,954 A | 10/1997 | Brigham |
| 5,693,622 A | 12/1997 | Wolff et al. |
| 5,703,055 A | 12/1997 | Felgner et al. |
| 5,763,270 A | 6/1998 | Eastman et al. |
| 5,935,565 A | 8/1999 | Besmer et al. |
| 6,034,072 A | 3/2000 | Ralston et al. |
| 6,040,295 A | 3/2000 | Rolland et al. |
| 6,080,728 A | 6/2000 | Mixson |
| 6,093,531 A | 7/2000 | Bjornson et al. |
| 6,261,549 B1 | 7/2001 | Fernández et al. |
| 6,326,198 B1 | 12/2001 | Emerson et al. |
| 6,710,035 B2 | 3/2004 | Felgner et al. |
| 6,734,014 B1 | 5/2004 | Hwu et al. |
| 6,875,748 B2 | 4/2005 | Manthorpe et al. |
| 6,911,530 B1 | 6/2005 | Willson et al. |
| 2005/0260767 A1 | 11/2005 | Clerici et al. |

FOREIGN PATENT DOCUMENTS

| | | |
|---|---|---|
| RU | 2238947 | 10/2004 |
| WO | WO 89/05345 | 6/1989 |
| WO | WO 90/06997 | 6/1990 |
| WO | WO 90/11092 | 10/1990 |
| WO | WO 92/05266 | 4/1992 |
| WO | WO 92/07573 | 5/1992 |
| WO | WO 92/14829 | 9/1992 |
| WO | WO 94/24983 | 11/1994 |
| WO | WO 94/29469 | 12/1994 |
| WO | WO-00/04050 | 1/2000 |
| WO | WO 03/045316 | * 6/2003 |
| WO | WO-2006/081171 | 8/2006 |

OTHER PUBLICATIONS

Babiuk et al. (2003) Induction of immune responses by DNA vaccines in large animals. Vaccine 21: 649-658.*
Donnelly et al. (1997) DNA Vaccines. Annu. Rev. Immunol. 15: 617-648.*
Finn, OJ (2003) Cancer vaccines: Between the idea and the reality. Nature Reviews Immunology 3: 630-641.*
McCluskie et al. (1999) Route and method of delivery of DNA vaccine influence immune responses in mice and non-human primates. Molecular Medicine 5: 287-300.*
Agadjanyan et al., Prototype Alzheimer's Disease Vaccine Using the Immunodominant B Cell Epitope from β-amyloid and Promiscuous T Cell Epitope Pan HLA DR-Binding Peptide, J. Immunol. 174:1580-86 (2005).
Anderson, W.F., Human Gene Therapy, Science 256(5058):808-13 (1992).
Berge et al., Pharmaceutical Salts, Journal of Pharmaceutical Sciences 66:1-19 (1977).
Caplen et al., Lipisome-mediated *CFTR* gene transfer to the nasal epithelium of patients with cystic fibrosis, Nature Med., 1:39-46 (1995).
Chen et al., Co-polymer of histidine and lysine markedly enhances transfection efficiency of liposomes, Gene Therapy 7(19):1698-705 (2000).
Chen et al., Activation of Toll-like Receptor 2 on Microglia Promotes Cell Uptake of Alzheimer Disease-associated Amyloid β Peptide, J. Biol. Chem. 281:3651-59 (2006).
Costa et al., Targeting Rare Populations of Murine Antigen-Specific T Lymphocytes by Retroviral Transduction for Potential Application in Gene Therapy for Autoimmune Disease, J. Immunol., 164:3581-90 (2000).
Curiel et al., High-Efficiency Gene Transfer Mediated by Adenovirus Coupled to DNA-Polylysine Complexes, Human Gene Therapy, 3:147-154 (1992).
Daëron et al., Regulation of high-affinity IgE receptor-mediated mast cell murine low-affinity IgG receptors, J Clin. Invest. 95(2): 577-85 (1995).
Davis et al., Direct Gene Transfer into Skeletal Muscle In Vivo: Factors Affecting Efficiency of Transfer and Stability of Expression, Human Gene Therapy 4:151-159 (1993).
Dickson et al., Microglia and cytokines in neurological disease, with special reference to AIDS and Alzheimer's disease, Glia 7:75-83 (1993).
Donnelly et al., Immunization with DNA, J Immunol Meth. 176:145-152 (1994).
Dzau et al., Gene therapy for cardiovascular disease, Trends in Biotechnology 11(5):205-10 (1993).

(Continued)

*Primary Examiner* — Anne-Marie Falk
(74) *Attorney, Agent, or Firm* — Foley & Lardner LLP

(57) ABSTRACT

Provided herein are compositions and methods for treating and/or preventing neurodegenerative disease, such as Alzheimer's disease. In particular aspects, compositions administered herein encode a cellular immune response element. The compositions may be prepared and administered in such a manner that the cellular immune response element coding sequence is expressed in the subject to which the composition is administered. The compositions include expression systems, delivery systems, and certain cellular immune response element genes.

10 Claims, 5 Drawing Sheets

OTHER PUBLICATIONS

Eck et al., Gene-based Therapy, in Goodman & Gilman's The Pharmacological Basis of Therapeutics, Ninth Edition, Hardman et al., eds., McGray-Hill, New York, Chapter 5, pp. 77-101, (1996).
Felgner et al., Lipofection: A highly efficient, lipid-mediated DNA-transfection procedure, Proc. Natl. Acad. Sci. 84:7413-7417 (1993).
Fillit et al., Elevated circulating tumor necrosis factor levels in Alzheimer's disease, Neurosci. Lett. 129:318-20 (1991).
Frenkel et al., Nasal vaccination with a proteosome-based adjuvant and glatiramer acetate clears β-amyloid in a mouse model of Alzheimer disease, J. Clin. Inves. 115:2423-33 (2005).
Ghochikyan et al., Generation and characterization of the humoral immune response to DNA immunization with a chimeric β-amyloid-interleukin-4 minigene, Eur J Immunol. 33(12):3232-3241 (2003).
Jaini et al., Gene-Based Intramuscular Interferon-β Therapy for Experimental Autoimmune Encephalomyelitis, Mol. Ther. 14(3):416-422 (2006).
Kaneda et al., Increased expression of DNA cointroduced with nuclear protein in adult rat liver, Science 243:375-378 (1989).
Kim et al., Effective Treatment of Established Murine Collagen-Induced Arthritis by Systemic Administration of Dendritic Cells Genetically Modified to Express IL-4, J. Immunol. 166(21):3499-3550 (2001).
Lesoon-Wood et al., Systemic Gene Therapy with p53 Reduces Growth and Metastases of a Malignant Human Breast Cancer in Nude Mice, Human Gene Therapy 6:395-405 (1995).
Luxembourg et al., Electroporation-based DNA immunization: translation to the clinic, Expert Opinion Biol. Ther. 7(11):1647-1664 (2007).
Luxembourg et al., Enhancement of immune responses to an HBV DNA vaccine by electroporation, Vaccine (24(21):4490-4493 (2006).
Mannino et al., Lipisome mediated gene transfer, Biotechniques 6:682-690 (1988).
McGeer et al., Anti-inflammatory agents as a therapeutic approach to Alzheimer's disease, Neurology 42:447-449 (1992).
Morita et al., Dendritic cells genetically engineered to express IL-4 inhibit murine collagen-induced arthritis, J. Clin. Invest., 17(21):1275-84 (2001).
Nakajima et al., Antigen-specific T cell-mediated gene therapy in collagen-induced arthritis, J. Clin. Invest., 17(21):1293-1310 (2001).
Nicolau et al., In vivo expression of rat insulin after intravenous administration of the lipisome-entrapped gene for rat insulin I, Proc. Natl. Acad. Sci USA 80:1068-1072 (1983).
Okura et al., Nonviral Aβ DNA vaccine therapy against Alzheimer's disease: Long-term effects and safety, PNAS USA 103(25):9619-24 (Epub Jun. 12, 2006).
Qu et al., $A\beta_{42}$ gene vaccination reduces brain amyloid plaque burden in transgenic mice, J. Neurol. Sci. 244(1-2):151-158 (2006).
Rabinovich et al., Recombinant Galectin-1 and Its Genetic Delivery Suppress Collagen-Induced Arthritis via T Cell Apoptosis J. Exp. Med., 19:385-98 (1999).
Raz et al., Intradermal gene immunization: The possible role of DNA uptake in the induction of cellular immunity to viruses, Pro. Natl. Acad. Sci. 91:9519-9523 (1994).
Recombinant DNA Advisory Committee Data Management Report, Human Gene Therapy 6: 535-548 (1994).
Romano et al., Latest Developments in Gene Transfer Technology: Achievements, Perspectives, and Controversies over Therapeutic Applications, Stem Cells, 18:19-39 (2000).
Rosenberg et al., Grafting Genetically Modified Cells to the Damaged Brain: Restorative Effects of NGF Expression, Science, 242:1575-1578 (1988).
Sato et al., Immunostimulatory DNA Sequences Necessary for Effective Intradermal Gene Immunization, Science 273: 352-354 (1996).
Seroogy et al., The application of gene therapy in autoimmune diseases, Gene Therapy, 7:9-13 (2000).
Shackleford et al., Construction of a clonable, infectious, and tumorigenic mouse mammary tumor virus provirus and a derivative genetic vector, Proc. Natl. Acad. Sci. U.S.A. 85:9655-9659 (1998).
Tang et al. Genetic immunization is a simple method for eliciting an immune response, Nature 356:152-154, (1992).
Tuohy et al., T cell design for therapy in autoimmune demyelinating disease, J. Neuroimmunol., 17(2):226-32 (2000).
Wagner et al., Transferring-polycation conjugates as carriers for DNA uptake into cells, Proc. Natl. Acad. Sci. USA 87(9):3410-4 (1990).
Weiner et al., Oral tolerance: mechanisms and applications. Introduction, NY Acad. Sci., vol. 778, p. xiii-xviii (1996).
Wilson, J.M., Vectors—shuttle vehicles for gene therapy, Clin. Exp. Immunol. 107 (Suppl. 1):31-32 (1997).
Wivel N.A., MD and Wilson, J.M., MD, PhD, Methods of Gene Delivery, Hematology/Oncology Clinics of North America, Gene Therapy, S.L. Eck, ed., 12(3):483-501 (1998).
Wolff et al., Grafting fibroblasts genetically modified to produce L-dopa in a rat model of Parkinson disease, Proc. Natl. Acad. Sci. USA 86:9011-9014 (1989).
Wolff et al., Direct gene transfer into mouse muscle in vivo, Science, 247, 1465-1468 (1990).
Wolff et al., Long-term persistence of plasmid DNA and foreign gone expression in mouse muscle, Hum. Mol. Genet. 1:363-69 (1992).
Wu, G.Y. and Wu, C.H., Receptor-mediated in Vitro Gene Transformation by a Soluble DNA Carrier System, J. Biol. Chem. 262(10):4429-32 (1987).
Xu et al., Gene Therapy with P53 and a Fragment of Thrombospondin I Inhibits Human Breast Cancer in Vivo, Molecular Genetics and Metabolism, 63:103-109 (1998).
Zhu et al., Systemic gene expression after intravenous DNA delilvery into adult mice, Science, 261:209-211 (1993).
International Preliminary Report on Patentability dated Aug. 11, 2009 in application PCT/US2008/052953.
International Search Report dated Sep. 16, 2008 in application PCT/US2008/52953.
Dasilva, et al., Immunization with amyloid-beta using GM-CSF and IL-4 reduces amyloid burden and alters plaque morphology, Neurobiology of Disease, 23:433-444 (2006).
Poliani, et al., Delivery to the central nervous system of a nonreplicative herpes simplex type 1 vector engineered with the interleukin 4 gene protects rhesus monkeys from hyperacute autoimmune encephalomyelitis, Human Gene Therapy, 12:905-920 (2001).
Supplemental Search Report dated Apr. 11, 2011 in EP Application No. 08728962.5.
Zhao, et al., Protective effects of an anti-inflammatory cytokine, interleukin-4, on motoneuron toxicity induced by activated microglia, Journal of Neurochemistry, 99:1176-1187 (2006).
Office Action cited in related Russian Patent Application No. 2009132196, dated Jan. 17, 2012.

* cited by examiner

Mixed DNA Vaccine Treated Mouse

Untreated Mouse

SEQUENCE LISTING

<160> NUMBER OF SEQ ID NOS: 20

<210> SEQ ID NO 1
<211> LENGTH: 614
<212> TYPE: DNA
<213> ORGANISM: Homo sapiens

<400> SEQUENCE: 1

```
gatcgttagc ttctcctgat aaactaattg cctcacattg tcactgcaaa tcgacaccta      60
ttaatgggtc tcacctccca actgcttccc cctctgttct tcctgctagc atgtgccggc     120
aactttgtcc acggacacaa gtgcgatatc accttacagg agatcatcaa aactttgaac     180
agcctcacag agcagaagac tctgtgcacc gagttgaccg taacagacat ctttgctgcc     240
tccaagaaca caactgagaa ggaaaccttc tgcagggctg cgactgtgct ccggcagttc     300
tacagccacc atgagaagga cactcgctgc ctgggtgcga ctgcacagca gttccacagg     360
cacaagcagc tgatccgatt cctgaaacgg ctcgacagga acctctgggg cctggcgggc     420
ttgaattcct gtcctgtgaa ggaagccaac cagagtacgt tggaaaactt cttggaaagg     480
ctaaagacga tcatgagaga gaaatattca aagtgttcga gctgaatatt ttaatttatg     540
agtttttgat agctttattt tttaagtatt tatatattta taactcatca taaaataaag     600
tatatataga atct                                                       614
```

<210> SEQ ID NO 2
<211> LENGTH: 459
<212> TYPE: DNA
<213> ORGANISM: Homo sapiens

<400> SEQUENCE: 2

```
caaacgcaga acgtttcaga gccatgagga tgcttctgca tttgagtttg ctagctcttg      60
gagctgccta cgtgtatgcc atcccacag aaattcccac aagtgcattg gtgaaagaga     120
ccttggcact gctttctact catcgaactc tgctgatagc caatgagact ctgaggattc     180
ctgttcctgt acataaaaat caccaactgt gcactgaaga aatcttttcag ggaataggca     240 cactggagag tcaaactgtg caaggggta ctgtggaaag actattcaaa aacttgtcct     300
taataaagaa atacattgac ggccaaaaaa aaaagtgtgg agaagaaaga cggagagtaa     360
accaattcct agactacctg caagagtttc ttggtgtaat gaacaccgag tggataatag     420
aaagttgaga ctaaactggt tgttgcagcc aaagataac                           459
```

<210> SEQ ID NO 3
<211> LENGTH: 1601
<212> TYPE: DNA
<213> ORGANISM: Homo sapiens

<400> SEQUENCE: 3

```
aaaccacaag acagacttgc aaaagaaggc atgcacagct cagcactgct ctgttgcctg      60
gtcctcctga ctggggtgag ggccagccca ggccagggca cccagtctga aacagctgc     120
```

```
acccacttcc caggcaacct gcctaacatg cttcgagatc tccgagatgc cttcagcaga      180
gtgaagactt tctttcaaat gaaggatcag ctggacaact tgttgttaaa ggagtccttg      240
ctggaggact ttaagggtta cctgggttgc caagccttgt ctgagatgat ccagttttac      300
ctggaggagg tgatgcccca agctgagaac caagacccag acatcaaggc gcatgtgaac      360
tccctggggg agaacctgaa gaccctcagg ctgaggctac ggcgctgtca tcgatttctt      420
ccctgtgaaa acaagagcaa ggccgtggag caggtgaaga atgcctttaa taagctccaa      480
gagaaaggca tctacaaagc catgagtgag tttgacatct tcatcaacta catagaagcc      540
tacatgacaa tgaagatacg aaactgagac atcagggtgg cgactctata gactctagga      600
cataaattag aggtctccaa aatcggatct ggggctctgg gatagctgac ccagccccct      660
gagaaacctt attgtacctc tcttatagaa tatttattac ctctgatacc tcaaccccca      720
tttctattta tttactgagc ttctctgtga acgatttaga aagaagccca atattataat      780
ttttttcaat atttattatt ttcacctgtt tttaagctgt ttccataggg tgacacacta      840
tggtatttga gtgttttaag ataaattata agttacataa gggaggaaaa aaaatgttct      900
ttggggagcc aacagaagct tccattccaa gcctgaccac gctttctagc tgttgagctg      960
ttttccctga cctccctcta atttatcttg tctctgggct tggggcttcc taactgctac     1020
aaatactctt aggaagagaa accagggagc ccctttgatg attaattcac cttccagtgt     1080
ctcggaggga ttcccctaac ctcattcccc aaccacttca ttcttgaaag ctgtggccag     1140
cttgttattt ataacaacct aaatttggtt ctaggccggg cgcggtggct cacgcctgta     1200
atcccagcac tttgggaggc tgaggcgggt ggatcacttg aggtcaggag ttcctaacca     1260
gcctggtcaa catggtgaaa ccccgtctct actaaaaata caaaaattag ccgggcatgg     1320
tggcgcgcac ctgtaatccc agctacttgg gaggctgagg caagagaatt gcttgaaccc     1380
aggagatgga agttgcagtg agctgatatc atgcccctgt actccagcct gggtgacaga     1440
gcaagactct gtctcaaaaa aataaaaata aaataaaatt tggttctaat agaactcagt     1500
tttaactaga atttattcaa ttcctctggg aatgttacat tgtttgtctg tcttcatagc     1560
agattttaat tttgaataaa taaatgtatc ttattcacat c                        1601

<210> SEQ ID NO 4
<211> LENGTH: 1270
<212> TYPE: DNA
<213> ORGANISM: Homo sapiens

<400> SEQUENCE: 4
ttcggcatcc gctcctcaat cctctcctgt tggcactggg cctcatggcg cttttgttga      60
ccacggtcat tgctctcact tgccttggcg gctttgcctc cccaggccct gtgcctccct     120
ctacagccct cagggagctc attgaggagc tggtcaacat cacccagaac cagaaggctc     180
cgctctgcaa tggcagcatg gtatggagca tcaacctgac agctggcatg tactgtgcag     240
ccctggaatc cctgatcaac gtgtcaggct gcagtgccat cgagaagacc cagaggatgc     300
tgagcggatt ctgcccgcac aaggtctcag ctggcagtt tccagcttg catgtccgag     360
acaccaaaat cgaggtggcc cagtttgtaa aggacctgct cttacattta aagaaacttt     420
ttcgcgaggg acggttcaac tgaaacttcg aaagcatcat tatttgcaga gacaggacct     480
gactattgaa gttgcagatt cattttttctt tctgatgtca aaaatgtctt gggtaggcgg     540
gaaggagggt tagggagggg taaaattcct tagcttagac ctcagccctgt gctgcccgtc     600
ttcagcctag ccgacctcag ccttcccctt gcccagggct cagcctggtg ggcctcctct     660
```

-continued

| | |
|---|---|
| gtccagggcc ctgagctcgg tggacccagg gatgacatgt ccctacaccc ctcccctgcc | 720 |
| ctagagcaca ctgtagcatt acagtgggtg ccccccttgc cagacatgtg gtgggacagg | 780 |
| gacccacttc acacacaggc aactgaggca gacagcagct caggcacact tcttcttggt | 840 |
| cttatttatt attgtgtgtt atttaaatga gtgtgtttgt caccgttggg gattggggaa | 900 |
| gactgtggct gctggcactt ggagccaagg gttcagagac tcagggcccc agcactaaag | 960 |
| cagtggaccc caggagtccc tggtaataag tactgtgtac agaattctgc tacctcactg | 1020 |
| gggtcctggg gcctcggagc ctcatccgag gcagggtcag gagagggca gaacagccgc | 1080 |
| tcctgtctgc cagccagcag ccagctctca gccaacgagt aatttattgt ttttcctcgt | 1140 |
| atttaaatat taaatatgtt agcaaagagt taatatatag aagggtacct tgaacactgg | 1200 |
| gggaggggac attgaacaag ttgtttcatt gactatcaaa ctgaagccag aaataaagtt | 1260 |
| ggtgacagat | 1270 |

<210> SEQ ID NO 5
<211> LENGTH: 1448
<212> TYPE: DNA
<213> ORGANISM: Homo sapiens

<400> SEQUENCE: 5

| | |
|---|---|
| gtgaccgagc ggcgcggacg gccgcctgcc ccctctgcca cctggggcgg tgcgggcccg | 60 |
| gagcccggag cccgggtagc gcgtagagcc ggcgcgatgc acgtgcgctc actgcgagct | 120 |
| gcggcgccgc acagcttcgt ggcgctctgg gcacccctgt tcctgctgcg ctccgccctg | 180 |
| gccgacttca gcctggacaa cgaggtgcac tcgagcttca tccaccggcg cctccgcagc | 240 |
| caggagcggc gggagatgca gcgcgagatc ctctccattt tgggcttgcc ccaccgcccg | 300 |
| cgcccgcacc tccagggcaa gcacaactcg gcacccgtgt tcatgctgga cctgtacaac | 360 |
| gccatggcgg tggaggaggg cggcgggccc ggcggccagg gcttctccta cccctacaag | 420 |
| gccgtcttca gtacccaggg ccccccctctg gccagcctgc aagatagcca tttcctcacc | 480 |
| gacgccgaca tggtcatgag cttcgtcaac ctcgtggaac atgacaagga attcttccac | 540 |
| ccacgctacc accatcgaga gttccggttt gatctttcca agatcccaga aggggaagct | 600 |
| gtcacggcag ccgaattccg gatctacaag gactacatcc gggaacgctt cgacaatgag | 660 |
| acgttccgga tcagcgtttta tcaggtgctc caggagcact gggcaggga tcggatctc | 720 |
| ttcctgctcg acagccgtac cctctgggcc tcggaggagg gctggctggt gtttgacatc | 780 |
| acagccacca gcaaccactg ggtggtcaat ccgcggcaca acctgggcct gcagctctcg | 840 |
| gtggagacgc tggatgggca gagcatcaac cccaagttgg cgggcctgat tgggcggcac | 900 |
| gggccccaga acaagcagcc cttcatggtg gctttcttca aggccacgga ggtccacttc | 960 |
| cgcagcatcc ggtccacggg gagcaaacag cgcagccaga accgctccaa gacgcccaag | 1020 |
| aaccaggaag ccctgcggat ggccaacgtg cagagaacga gcagcagcga ccagaggcag | 1080 |
| gcctgtaaga agcacgagct gtatgtcagc ttccgagacc tgggctggca ggactggatc | 1140 |
| atcgcgcctg aaggctacgc cgcctactac tgtgaggggg agtgtgcctt ccctctgaac | 1200 |
| tcctacatga acgccaccaa ccacgccatc gtgcagacgc tggtccactt catcaacccg | 1260 |
| gaaacggtgc ccaagccctg ctgtgcgccc acgcagctca atgccatctc cgtcctctac | 1320 |
| ttcgatgaca gctccaacgt catcctgaag aaatacagaa acatggtggt ccgggcctgt | 1380 |
| ggctgccact agctcctccg agaattcaga ccctttgggg ccaagttttt ctggatcctc | 1440 |
| cattgctc | 1448 |

<210> SEQ ID NO 6
<211> LENGTH: 918
<212> TYPE: DNA
<213> ORGANISM: Homo sapiens

<400> SEQUENCE: 6

```
ggtgaaagaa agccctaacc agttttctgt cttgtttctg ctttctccct acagttccac      60
caggtgagaa gagtgatgac catccttttc cttactatgg ttatttcata ctttggttgc     120
atgaaggctg cccccatgaa agaagcaaac atccgaggac aaggtggctt ggcctaccca     180
ggtgtgcgga cccatgggac tctggagagc gtgaatgggc ccaaggcagg ttcaagaggc     240
ttgacatcat tggctgacac tttcgaacac gtgatagaag agctgttgga tgaggaccag     300
aaagttcggc ccaatgaaga aaacaataag gacgcagact tgtacacgtc cagggtgatg     360
ctcagtagtc aagtgccttt ggagcctcct ctttctcttc tgctggagga atacaaaaat     420
tacctagatg ctgcaaacat gtccatgagg gtccggcgcc actctgaccc tgcccgccga     480
ggggagctga gcgtgtgtga cagtattagt gagtgggtaa cggcggcaga caaaaagact     540
gcagtggaca tgtcgggcgg gacggtcaca gtccttgaaa aggtccctgt atcaaaaggc     600
caactgaagc aatacttcta cgagaccaag tgcaatccca tgggttacac aaaagaaggc     660
tgcaggggca tagacaaaag gcattggaac tcccagtgcc gaactaccca gtcgtacgtg     720
cgggccctta ccatggatag caaaaagaga attggctggc gattcataag gatagacact     780
tcttgtgtat gtacattgac cattaaaagg ggaagatagt ggatttatgt tgtatagatt     840
agattatatt gagacaaaaa ttatctattt gtatatatac ataacagggt aaattattca     900
gttaagaaaa aaataatt                                                   918
```

<210> SEQ ID NO 7
<211> LENGTH: 726
<212> TYPE: DNA
<213> ORGANISM: Homo sapiens

<400> SEQUENCE: 7

```
atgtccatgt tgttctacac tctgatcaca gcttttctga tcggcataca ggcggaacca      60
cactcagaga gcaatgtccc tgcaggacac accatccccc aagcccactg gactaaactt     120
cagcattccc ttgacactgc ccttcgcaga gcccgcagcg ccccggcagc ggcgatagct     180
gcacgcgtgg cggggcagac ccgcaacatt actgtggacc ccaggctgtt taaaaagcgg     240
cgactccgtt caccccgtgt gctgtttagc acccagcctc ccgtgaagc tgcagacact     300
caggatctgg acttcgaggt cggtggtgct gccccttca acaggactca caggagcaag     360
cggtcatcat cccatcccat cttccacagg ggcgaattct cggtgtgtga cagtgtcagc     420
gtgtgggttg gggataagac caccgccaca gacatcaagg gcaaggaggt gatggtgttg     480
ggagaggtga acattaacaa cagtgtattc aaacagtact ttttgagac caagtgccgg     540
gacccaaatc ccgttgacag cgggtgccgg ggcattgact caaagcactg gaactcatat     600
tgtaccacga ctcacacctt tgtcaaggcg ctgaccatgg atggcaagca ggctgcctgg     660
cggtttatcc ggatagatac ggcctgtgtg tgtgtgctca gcaggaaggc tgtgagaaga     720
gcctag                                                                726
```

<210> SEQ ID NO 8
<211> LENGTH: 1319
<212> TYPE: DNA
<213> ORGANISM: Homo sapiens -continued

<400> SEQUENCE: 8

```
cgagagcacg cggagcagcg tgcgcggggg ccccgggaga cggcggcggt ggcggcgcgg      60
gcagagcaag gacgcggcgg atcccactcg cacagcagcg cactcggtgc cccgcgcagg     120
gtcgcgatgc tgcccggttt ggcactgctc ctgctggccg cctggacggc tcgggcgctg     180
gaggtaccca ctgatggtaa tgctggcctg ctggctgaac cccagattgc catgttctgt     240
ggcagactga acatgcacat gaatgtccag aatgggaagt gggattcaga tccatcaggg     300
accaaaacct gcattgatac caaggaaggc atcctgcagt attgccaaga agtctaccct     360
gaactgcaga tcaccaatgt ggtagaagcc aaccaaccag tgaccatcca gaactggtgc     420
aagcggggcc gcaagcagtg caagacccat ccccactttg tgattcccta ccgctgctta     480
gttggtgagt ttgtaagtga tgcccttctc gttcctgaca agtgcaaatt cttacaccag     540
gagaggatgg atgtttgcga aactcatctt cactggcaca ccgtcgccaa agagacatgc     600
agtgagaaga gtaccaactt gcatgactac ggcatgttgc tgccctgcgg aattgacaag     660
ttccgagggg tagagtttgt gtgttgccca ctggctgaag aaagtgacaa tgtggattct     720
gctgatgcgg aggaggatga ctcggatgtc tggtggggcg gagcagacac agactatgca     780
gatgggagtg aagacaaagt agtagaagta gcagaggagg aagaagtggc tgaggtggaa     840
gaagaagaag ccgatgatga cgaggacgat gaggatggtg atgaggtaga ggaagaggct     900
gaggaaccct acgaagaagc cacagagaga accaccagca ttgccaccac caccaccacc     960
accacagagt ctgtgaagag ggtggttcga gagaagtggt ataaggaagt acattctggc    1020
caggcacgat ggctcatgct gtaatcccag cactttggga ggccgaggtg ggtgcatcac    1080
ctgaggtcag gagtttgaga ccagcctggc caacatggtg aaaccccctcg ctactaaaaa    1140
tacaaaaatt agccgggcgt ggtggcacac acctgtggtc ccagctactc gggaggctga    1200
agcaggagaa tcgcttgaac ccgggagacg gaggttgcag taagccgagt tcactccatt    1260
gtactctagc ctgggtgaca gagcgagatt cgtctcaaaa aaaaaaaaaa aaaaaaaa      1319
```

<210> SEQ ID NO 9
<211> LENGTH: 1186
<212> TYPE: DNA
<213> ORGANISM: Homo sapiens

<400> SEQUENCE: 9

```
ggacgtcctt ccccaggagc cgactggcca atcacaggca ggaagatgaa ggttctgtgg      60
gctgcgttgc tggtcacatt cctgcaggga tgccaggcca aggtggagca agcggtggag     120
acagagccgg agcccgagct gcgccagcag accgagtggc agagcggcca cgctgggaa     180
ctggcactgg gtcgcttttg ggattacctg cgctgggtgc agacactgtc tgagcaggtg     240
caggaggagc tgctcagctc ccaggtcacc caggaactga gggcgctgat ggacgagacc     300
atgaaggagt tgaaggccta caaatcggaa ctggaggaac aactgacccc ggtggcggag     360
gagacgcggg cacggctgtc caaggagctg caggcggcgc aggcccggct gggcgcggac     420
atggaggacg tgtgcggccg cctggtgcag taccgcggcg aggtgcaggc catgctcggc     480
cagagcaccg aggagctgcg ggtgcgcctc gcctcccacc tgcgcaagct gcgtaagcgg     540
ctcctccgcg atgccgatga cctgcagaag cgcctggcag tgtaccaggc cggggcccgc     600
gagggcgccg agcgcggcct cagcgccatc cgcgagcgcc tggggcccct ggtggaacag     660
ggccgcgtgc gggccgccac tgtgggctcc ctggccggcc agccgctaca ggagcgggcc     720
caggcctggg gcgagcggct gcgcgcgcgg atggaggaga tgggcagccg gacccgcgac     780
```

```
cgcctggacg aggtgaagga gcaggtggcg gaggtgcgcg ccaagctgga ggagcaggcc    840
cagcagatac gcctgcaggc cgaggccttc caggcccgcc tcaagagctg gttcgagccc    900
ctggtggaag acatgcagcg ccagtgggcc gggctggtgg agaaggtgca ggctgccgtg    960
ggcaccagcg ccgcccctgt gcccagcgac aatcactgaa cgccgaagcc tgcagccatg   1020
cgaccccacg ccaccccgtg cctcctgcct ccgcgcagcc tgcagcggga ccctgtcc    1080 ccgcccagc cgtcctcctg gggtggaccc tagtttaata aagattcacc aagtttcacg    1140
caaaaaaaaa aaaaaaaaa aaaaaaaaa aaaaaaaaaa aaaaac                   1186

<210> SEQ ID NO 10
<211> LENGTH: 954
<212> TYPE: DNA
<213> ORGANISM: Homo sapiens

<400> SEQUENCE: 10
atgaaggttc tgtgggctgc gttgctggtc acattcctgg caggatgcca ggccaaggtg     60
gagcaagcgg tggagacaga gccggagccc gagctgcgcc agcagaccga gtggcagagc    120
ggccagcgct gggaactggc actgggtcgc ttttgggatt acctgcgctg ggtgcagaca    180
ctgtctgagc aggtgcagga ggagctgctc agctcccagg tcacccagga actgagggcg    240
ctgatggacg agaccatgaa ggagttgaag gcctacaaat cggaactgga ggaacaactg    300
accccggtgg cggaggagac gcgggcacgg ctgtccaagg agctgcaggc ggcgcaggcc    360
cggctgggcg cggacatgga ggacgtgtgc ggccgcctgg tgcagtaccg cggcgaggtg    420
caggccatgc tcggccagag caccgaggag ctgcgggtgc gcctcgcctc ccacctgcgc    480
aagctgtgta gcggctcct ccgcgatgcc gatgacctgc agaagtgcct ggcagtgtac    540
caggccgggg cccgcgaggg cgccgagcgc ggcctcagcg ccatccgcga gcgcctgggg    600
cccctggtgg aacagggccg cgtgcgggcc gccactgtgg gctccctggc cggccagccg    660
ctacaggagc gggcccaggc ctgggcgag cggctgcgcg cgcggatgga ggagatgggc    720
agccggaccc cgaccgcct ggacgaggtg aaggagcagg tggcggaggt gcgcgccaag    780
ctggaggagc aggcccagca gatacgcctg caggccgagg ccttccaggc ccgcctcaag    840
agctggttcg agcccctggt ggaagacatg cagcgccagt gggccgggct ggtggagaag    900
gtgcaggctg ccgtgggcac cagcgccgcc cctgtgccca gcgacaatca ctga         954

<210> SEQ ID NO 11
<211> LENGTH: 153
<212> TYPE: PRT
<213> ORGANISM: Homo sapiens

<400> SEQUENCE: 11

Met Gly Leu Thr Ser Gln Leu Leu Pro Pro Leu Phe Phe Leu Leu Ala
 1               5                  10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95
```

```
Phe His Arg His Lys Gln Leu Ile Arg Phe Leu Lys Arg Leu Asp Arg
                100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
130                 135                 140

Arg Glu Lys Tyr Ser Lys Cys Ser Ser
145                 150

<210> SEQ ID NO 12
<211> LENGTH: 134
<212> TYPE: PRT
<213> ORGANISM: Homo sapiens

<400> SEQUENCE: 12

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
                100                 105                 110

Asn Gln Phe Leu Asp Tyr Leu Gln Glu Phe Leu Gly Val Met Asn Thr
            115                 120                 125

Glu Trp Ile Ile Glu Ser
        130

<210> SEQ ID NO 13
<211> LENGTH: 178
<212> TYPE: PRT
<213> ORGANISM: Homo sapiens

<400> SEQUENCE: 13

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
```

```
                130                 135                 140
Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 14
<211> LENGTH: 132
<212> TYPE: PRT
<213> ORGANISM: Homo sapiens

<400> SEQUENCE: 14

Met Ala Leu Leu Leu Thr Thr Val Ile Ala Leu Thr Cys Leu Gly Gly
  1               5                  10                  15

Phe Ala Ser Pro Gly Pro Val Pro Ser Thr Ala Leu Arg Glu Leu
                 20                  25                  30

Ile Glu Glu Leu Val Asn Ile Thr Gln Asn Gln Lys Ala Pro Leu Cys
                 35                  40                  45

Asn Gly Ser Met Val Trp Ser Ile Asn Leu Thr Ala Gly Met Tyr Cys
             50                  55                  60

Ala Ala Leu Glu Ser Leu Ile Asn Val Ser Gly Cys Ser Ala Ile Glu
 65                  70                  75                  80

Lys Thr Gln Arg Met Leu Ser Gly Phe Cys Pro His Lys Val Ser Ala
                 85                  90                  95

Gly Gln Phe Ser Ser Leu His Val Arg Asp Thr Lys Ile Glu Val Ala
                100                 105                 110

Gln Phe Val Lys Asp Leu Leu Leu His Leu Lys Lys Leu Phe Arg Glu
            115                 120                 125

Gly Arg Phe Asn
    130

<210> SEQ ID NO 15
<211> LENGTH: 431
<212> TYPE: PRT
<213> ORGANISM: Homo sapiens

<400> SEQUENCE: 15

Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
                 20                  25                  30

Leu Asp Asn Glu Val His Ser Ser Phe Ile His Arg Arg Leu Arg Ser
             35                  40                  45

Gln Glu Arg Arg Glu Met Gln Arg Glu Ile Leu Ser Ile Leu Gly Leu
             50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
        130                 135                 140
```

```
Glu Phe Phe His Pro Arg Tyr His Arg Glu Arg Phe Asp Leu
145                 150                 155                 160

Ser Lys Ile Pro Glu Gly Ala Val Thr Ala Ala Glu Phe Arg Ile
            165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
            245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
            405                 410                 415

Leu Lys Lys Tyr Arg Asn Met Val Val Arg Ala Cys Gly Cys His
420                 425                 430

<210> SEQ ID NO 16
<211> LENGTH: 247
<212> TYPE: PRT
<213> ORGANISM: Homo sapiens

<400> SEQUENCE: 16

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95
```

```
Ser Ser Gln Val Pro Leu Glu Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 17
<211> LENGTH: 241
<212> TYPE: PRT
<213> ORGANISM: Homo sapiens

<400> SEQUENCE: 17

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
                20                  25                  30

Pro Gln Ala His Trp Thr Lys Leu Gln His Ser Leu Asp Thr Ala Leu
            35                  40                  45

Arg Arg Ala Arg Ser Ala Pro Ala Ala Ile Ala Ala Arg Val Ala
        50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
                100                 105                 110

Phe Asn Arg Thr His Arg Ser Lys Arg Ser Ser Ser His Pro Ile Phe
            115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220
```

```
Ile Asp Thr Ala Cys Val Cys Val Leu Ser Arg Lys Ala Val Arg Arg
225                 230                 235                 240

Ala
```

<210> SEQ ID NO 18
<211> LENGTH: 305
<212> TYPE: PRT
<213> ORGANISM: Homo sapiens

<400> SEQUENCE: 18

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Arg Thr Thr Ser Ile
            260                 265                 270

Ala Thr Thr Thr Thr Thr Thr Thr Glu Ser Val Glu Glu Val Val Arg
        275                 280                 285

Glu Lys Trp Tyr Lys Glu Val His Ser Gly Gln Ala Arg Trp Leu Met
    290                 295                 300

Leu
305
```

<210> SEQ ID NO 19
<211> LENGTH: 317
<212> TYPE: PRT
<213> ORGANISM: Homo sapiens

<400> SEQUENCE: 19

```
Met Lys Val Leu Trp Ala Ala Leu Leu Val Thr Phe Leu Ala Gly Cys
  1               5                  10                  15

Gln Ala Lys Val Glu Gln Ala Val Glu Thr Glu Pro Glu Pro Glu Leu
             20                  25                  30

Arg Gln Gln Thr Glu Trp Gln Ser Gly Gln Arg Trp Glu Leu Ala Leu
         35                  40                  45

Gly Arg Phe Trp Asp Tyr Leu Arg Trp Val Gln Thr Leu Ser Glu Gln
 50                  55                  60

Val Gln Glu Glu Leu Leu Ser Ser Gln Val Thr Gln Glu Leu Arg Ala
 65                  70                  75                  80

Leu Met Asp Glu Thr Met Lys Glu Leu Lys Ala Tyr Lys Ser Glu Leu
                 85                  90                  95

Glu Glu Gln Leu Thr Pro Val Ala Glu Thr Arg Ala Arg Leu Ser
             100                 105                 110

Lys Glu Leu Gln Ala Ala Gln Ala Arg Leu Gly Ala Asp Met Glu Asp
         115                 120                 125

Val Cys Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                 165                 170                 175

Leu Ala Val Tyr Gln Ala Gly Ala Arg Glu Gly Ala Glu Arg Gly Leu
             180                 185                 190

Ser Ala Ile Arg Glu Arg Leu Gly Pro Leu Val Glu Gln Gly Arg Val
         195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                 245                 250                 255

Val Arg Ala Lys Leu Glu Glu Gln Ala Gln Gln Ile Arg Leu Gln Ala
             260                 265                 270

Glu Ala Phe Gln Ala Arg Leu Lys Ser Trp Phe Glu Pro Leu Val Glu
         275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 20
<211> LENGTH: 317
<212> TYPE: PRT
<213> ORGANISM: Homo sapiens

<400> SEQUENCE: 20

Met Lys Val Leu Trp Ala Ala Leu Leu Val Thr Phe Leu Ala Gly Cys
  1               5                  10                  15

Gln Ala Lys Val Glu Gln Ala Val Glu Thr Glu Pro Glu Pro Glu Leu
             20                  25                  30

Arg Gln Gln Thr Glu Trp Gln Ser Gly Gln Arg Trp Glu Leu Ala Leu
         35                  40                  45

Gly Arg Phe Trp Asp Tyr Leu Arg Trp Val Gln Thr Leu Ser Glu Gln
 50                  55                  60
```

-continued

```
Val Gln Glu Glu Leu Leu Ser Ser Gln Val Thr Gln Glu Leu Arg Ala
 65                  70                  75                  80

Leu Met Asp Glu Thr Met Lys Glu Leu Lys Ala Tyr Lys Ser Glu Leu
                 85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
        130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
            165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
            245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
            290                 295                 300

Val Gly Thr Ser Ala Ala Pro Val Pro Ser Asp Asn His
305                 310                 315
```

TREATMENT AND PREVENTION OF NEURODEGENERATIVE DISEASES USING GENE THERAPY

CROSS-REFERENCE TO RELATED APPLICATIONS

The present invention claims the priority of application Ser. No. 60/900,138, filed on Feb. 6, 2007.

FIELD OF THE INVENTION

Provided herein are compositions and methods for treatment and/or prevention of neurodegenerative diseases such as Alzheimer's disease. In certain aspects, the compositions and methods relate to adoptive cellular therapies and DNA immunization.

BACKGROUND OF THE INVENTION

Neuroinflammation is associated with Alzheimer's disease (AD) pathology (Chen, K. et al., 281 Peptide J. Biol. Chem. 3651-59 (2006) and Frenkel, D. et al., 115 J. Clin. Inves. 2423-33 (2005)). Neuroinflammation involves an accumulation of a large number of activated microglia and astrocytes as well as small numbers of T cells, mostly adhering to postcapillary venules (Agadjanyan, M. G. et al., 174 J. Immunol. 1580-86 (2005); Dickson, D. et al., 7 Glia 75-83 (1993); and Fillit, H. et al., 129 Neurosci. Lett. 318-20 (1991)). Both microglia and astrocytes have been shown to generate β-amyloid protein (Aβ), one of the main pathologic features of AD. Aβ itself has been shown to act as a pro-inflammatory agent causing the activation of many inflammatory components. Accompanying biochemical alterations include the appearance or up-regulation of numerous molecules characteristic of inflammation and free radical attack. Particularly important may be the complement proteins, acute phase reactants and inflammatory cytokines. Patients that take non-steroidal anti-inflammatory drugs have a lower risk of AD than those who do not. These results have led to increased interest in pursuing anti-inflammatory therapy for AD (Fillit, H. 1991).

SUMMARY OF THE INVENTION

Although neurodegenerative diseases such as Alzheimer's disease are not classically considered mediated by inflammation or the immune system, in some instances the immune system plays an important role in degenerative processes. Immunotherapeutic approaches designed to induce a humoral immune response have been previously developed for treating AD. Those studies led to human trials that resulted in both beneficial and adverse effects. In animal models, it has been shown that immunotherapy designed to induce a cellular immune response may be of benefit in central nervous system injury, although T cells may have either a beneficial or detrimental effect depending on the type of T cell response induced. These studies provide a new avenue to explore immune system-based therapy of neurodegenerative diseases.

The adaptive immune system can be broadly classified into two types of responses, cellular and humoral (antibody) types of responses. Among cellular responses, three main types or classes of immune response have been identified that play a crucial role in understanding the mechanisms of inflammatory process regulation, e.g., Th1 response (involving for example, IFN-γ) in contrast with Th2 or Th3 responses (involving for example, IL-4, IL-10, IL-13 and TGF-β). The different classes of T cell responses have important implications for developing a vaccination strategy for Alzheimer's disease.

Provided herein include compositions and methods for treatment and/or prevention of neurodegenerative diseases such as Alzheimer's disease. In certain aspects, the compositions and methods relate to DNA vaccines and adoptive cellular gene therapies to treat or ameliorate neurodegenerative disease. In certain particular aspects, the compositions and methods relate to DNA vaccines encoding a cellular immune response element such as a Th2 or Th3 cytokine.

In one aspect, a method is provided for treating or ameliorating neurodegenerative disease which includes administering a composition that induces a cellular immune response. In another aspect, a method is provided for treating or ameliorating neurodegenerative disease by administering a composition that induces a cellular immune response by administering a composition which includes a cellular immune response element; preferably the cellular immune response element is a protein, peptide, nucleic acid or polynucleotide. In a related aspect, also provided is a method of treating or ameliorating neurodegenerative disease which includes administering two or more; three or more; four or more; five or more; or six or more cellular immune response elements. In another aspect, also provided is a method of manufacturing a composition for treatment or prophylaxis of neurodegenerative disease which may include preparing a polynucleotide or fragment thereof with a promoter/enhancer transcriptionally linked to a sequence encoding a cellular immune response element gene or fragment thereof. In a related aspect, provided is a method of preparing a composition for expression of a cellular immune response element polynucleotide or fragment thereof in a subject which includes preparing a polynucleotide with a promoter/enhancer transcriptionally linked to a sequence encoding a cellular immune response element gene or fragment thereof; and combining the transfection facilitating material with the polynucleotide. Also provided are compositions and methods for administration to a mammal, preferably a human. In another aspect, a composition may include a pharmaceutically acceptable carrier and a polynucleotide including a sequence encoding a cellular immune response element polypeptide. In certain aspects, a kit is provided which may include a container suitable for holding a pharmaceutical for administration to a subject; preferably a human, a polynucleotide including a sequence encoding a cellular immune response element polypeptide, a pharmaceutically acceptable carrier, and a label affixed to the container or a package insert. In yet other aspects, provided are methods of administering a polypeptide homologous to a cellular immune response element polypeptide or fragment thereof.

In certain embodiments, a composition is provided that induces a cellular immune response element. The methods and compositions may include a protein, nucleic acid or polynucleotide; preferably the polynucleotide and/or nucleic acid is DNA or RNA; preferably the polynucleotide is circular DNA; preferably the polynucleotide is a plasmid; preferably the polynucleotide includes a promoter/enhancer transcriptionally linked to the sequence encoding a cellular immune response element gene; preferably the polynucleotide includes an origin of replication (ORI); preferably the polynucleotide includes a multiple cloning site (MCS); preferably the promoter is suitable for expression in eukaryotic cells; in some preferable embodiments, the polynucleotide is a vector; preferably a viral vector; in other preferable embodiments, the polynucleotide is RNA; preferably the polynucleotide is double stranded RNA; preferably the polynucleotide is short interfering RNA (siRNA); or preferably more than one composition that reduces inflammation can be administered simultaneously. In some embodiments a single cellular immune response element is on a single polynucleotide or plasmid; in other embodiments more than one cellular immune response element may be on a single polynucleotide or plasmid. In yet other embodiments, a single polynucleotide or plasmid includes one or more cellular immune response element and further includes one or more polypeptides known to treat or ameliorate the effects of a neurodegenerative disease or fragments thereof (i.e., brain-derived neurotrophic factor (BDNF), nerve growth factor (NGF), β-amyloid, β-amyloid peptides 1-42 (β-amyloid$_{1-42}$), apolipoprotein E (ApoE) or ApoE-2.

Other embodiments relate to administration of proteins, peptides and/or polypeptides of a cellular immune response element. In other embodiments, methods of administration of nucleic acids, and/or polynucleotides encoding cellular immune response element polypeptides are provided. The compositions may be prepared and administered in such a manner that a cellular immune response element polypeptide is expressed in a subject to which the composition is administered. The compositions may include expression systems, delivery systems, and coding sequences of immunoregulatory genes such as anti-inflammatory cytokines, cytokine agonists or anti-TNF antibodies. Preferably, the cellular immune response element of the methods and compositions increases a gene that decreases inflammation; preferably increasing gene expression is by up-regulating expression; preferably the gene that decreases inflammation is a Th2 cytokine; preferably the Th2 cytokine is IL-4, IL-5, IL-10, IL-13, or TGF-β; in other preferable embodiments, the composition including a cellular immune response element inhibits or attenuates a gene that increases inflammation; preferably the gene that increases inflammation is a Th1 cytokine; preferably attenuating gene expression is by down-regulating expression; preferably the Th1 cytokine is IL-2, IL-12, or TNFα; in some embodiments, the composition affects regulation by stimulating expression or producing a gene that decreases inflammation whereas in other embodiments, the composition affects regulation by inhibiting expression of a gene that increases stimulation such as a Th1 antagonist.

In certain embodiments, the cellular immune response element includes a gene or protein encoding an autoantigen, an autoimmune inflammation reducing cytokine, an antagonist to an autoimmune inflammation increasing cytokine, or a gene that induces anergy or fragments thereof; preferably, the cellular immune response element is, or is homologous to, interleukin (IL)-4, IL-5, IL-10, IL-13, transforming growth factor-beta (TGF-β) or fragments thereof.

In preferred embodiments, a cellular immune response element is further administered with a nucleic acid or protein encoding a polypeptide that further treats and/or ameliorates the effects of a neurodegenerative disease or fragments thereof; preferably, the additional gene or protein encoding a polypeptide is, or is homologous to, brain-derived neurotrophic factor (BDNF), nerve growth factor (NGF), β-amyloid, β-amyloid peptides 1-42 (β-amyloid$_{1-42}$), apolipoprotein E (ApoE) or ApoE-2.

In other preferred embodiments, the compositions and methods inducing a cellular immune response include delivery by adoptive cellular gene therapy. Preferably, the type of cell used for adoptive cellular therapy is autologous or non-autologous; preferably the type of cell used for adoptive cellular gene therapy is a T cell, an antigen presenting cell, a fibroblast or a stem cell; preferably the type of cell used for adoptive cellular gene therapy is a dendritic cell, NIH3T3 cell, non-autologous stem cells such as cells from American Type Culture Collection (ATCC) or an autologous stem cell.

In certain embodiments, polynucleotides described herein are administered to a patient with a pharmaceutically acceptable carrier. In certain embodiments, the polynucleotide includes a eukaryotic promoter; preferably the eukaryotic promoter provides expression in a human. In certain embodiments, the polynucleotide is a plasmid complexed with a promoter/enhancer transcriptionally linked to a sequence encoding a cellular immune response element. In certain embodiments, the polynucleotide is a viral vector. In certain embodiments, the polynucleotide is administered with a lipofection reagent. In certain embodiments, the methods may include one or more methods of administering the compositions provided herein selected from the group consisting of intravenously, intranasally, subcutaneously, by injection, by inhalation and by gene gun.

In certain preferred embodiments of the methods provided herein, the polynucleotide including a sequence encoding a cellular immune response element polypeptide or fragment thereof is administered to a mammal; more preferably the mammal is a human; preferably the polynucleotide including a sequence encoding a cellular immune response element gene or fragment thereof is administered with a transfection facilitating material; preferably the transfection facilitating material includes a lipid; preferably the polynucleotide is administered in a pharmaceutically acceptable carrier; in certain preferred embodiments the polynucleotide is administered by viral transduction; preferably the polynucleotide is administered by gene gun; preferably the polynucleotide is administered by inhalation; or preferably the polynucleotide is administered by injection, or preferably subcutaneous injection or preferably intramuscular injection.

In certain embodiments, compositions include a polynucleotide including a sequence encoding cellular immune response element polypeptide or fragment thereof; preferably the composition includes a pharmaceutically acceptable carrier; preferably the composition includes a transfection facilitating material, preferably the transfection facilitating material includes a lipid; preferably the composition is administered with an adjuvant; preferably the composition is suitable for injection into a mammal, preferably the mammal is a human; preferably the composition is suitable for inhalation by a mammal, preferably the mammal is a human; preferably the composition is enclosed in a pharmaceutically acceptable carrier, preferably the pharmaceutically acceptable carrier has a label indicating the contents therein and a statement regarding administration of the polynucleotide; preferably the composition includes a package insert, preferably the package insert includes statements regarding the contents of the composition, more preferably the package insert includes statements regarding dosing information.

As used herein, the term "antigen" refers broadly to any composition to which an individual can generate an immune response. "Antigen" as used herein refers broadly to a molecule that contains at least one antigenic determinant to which the immune response may be directed. The immune response may be cell mediated or humoral or both. As well known in the art, an antigen may be protein in nature, carbohydrate in nature, lipid in nature, nucleic acid in nature, or combinations of these biomolecules. For example, an antigen may include non-natural molecules such as polymers and the like. Antigens include self antigens and foreign antigens such as antigens produced by another animal or antigens from an infectious agent. Infectious agent antigens may be bacterial, viral, fungal, protozoan, and the like.

As used herein, the term "autologous" when used in referenced to removing cells from a subject, possibly altering the cells or preserving the cells and reinfusing the cells back into the subject.

As used herein, the term "coding region" or "coding sequence" refers to a nucleic acid sequence, its complement, or a part thereof, which encodes a particular gene product or a fragment thereof for which expression is desired, according to the normal base pairing and codon usage relationships. Coding sequences include exons in genomic DNA or immature primary RNA transcripts, which are joined together by the cell's biochemical machinery to provide a mature mRNA. The anti-sense strand is the complement of such a nucleic acid, and the encoding sequence can be deduced from there. The coding sequence is placed in relationship to transcriptional control elements and to translational initiation and termination codons so that a proper length transcript will be produced and will result in translation in the appropriate reading frame to produce a functional desired product.

The term "complement" "complementary" or "complementarity" as used herein with reference to polynucleotides (i.e., a sequence of nucleotides such as an oligonucleotide or a target nucleic acid) according to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain nucleotides not commonly found in natural nucleic acids may be included in the nucleic acids described herein; these include, for example, inosine, 7-deazaguanine, Locked Nucleic Acids (LNA), and Peptide Nucleic Acids (PNA). A complement sequence can also be a sequence of RNA complementary to the DNA sequence or its complement sequence, and can also be a cDNA. Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Complementarity may be "partial" in which only some of the nucleotide bases of two nucleic acid strands are matched according to the base pairing rules. Complementarity may be "complete" or "total" where all of the nucleotide bases of two nucleic acid strands are matched according to the base pairing rules. Complementarity may be absent where none of the nucleotide bases of two nucleic acid strands are matched according to the base pairing rules. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

As used herein, the term "substantially complementary" refers to two sequences that hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

As used herein, the term "dendritic cell" (DC) refers to an antigen presenting cell (APC) which can be derived from a hematopoietic stem cell. DC can be obtained from many lymphoid and non lymphoid tissues, as well as peripheral blood and bone marrow. Hematopoietic stem cells such as CD34+ cells in humans can be artificially differentiated into DC in vitro. The dendritic cell has a characteristic morphology with thin sheets (lamellipodia) extending from the dendritic cell body in several directions. Several phenotypic criteria are also typical, but can vary depending on the source of the dendritic cell. These include high levels of MHC molecules and costimulatory molecules (e.g., B7-1 and B7-2), a lack of markers specific for granulocytes, NK cells, B cells, and T cells. In the mouse, some (but not all) dendritic cells express 33D1 (DC from spleen and Peyer's patch, but not skin or thymic medulla), NLDC145 (DC in skin and T-dependent regions of several lymphoid organs and CD11C (Cd11c also reacts with macrophage). Dendritic cells are able to initiate primary T cell responses in vitro and in vivo. These responses are antigen specific. Dendritic cells direct a strong mixed leukocyte reaction (MLR) compared to peripheral blood leukocytes, splenocytes, B cells and monocytes.

As used herein, the term "expression" refers to the biological production of a product encoded by a coding sequence. In most cases a DNA sequence, including the coding sequence, is transcribed to form a messenger RNA (mRNA). Messenger-RNA is translated to form a polypeptide product which has biological activity. However in some cases, an RNA product may have the relevant activity and would thus be regarded as a gene product. Expression may involve further processing steps of the transcription RNA product, such as splicing to remove introns, and/or post-translational processing of a polypeptide product.

As used herein, terms relating to immunological tolerance refers to the acquisition of unresponsiveness to self-antigens. The ability to differentiate self-antigens and non-self-antigens is essential to the preservation of the host. Immunological tolerance is further described in Seroogy, C. M., et al., Gene Therapy, vol. 7, p. 9-13 (2000); Costa, G. L., et al., J. Immunol., vol. 164, p. 3581-90 (2000); and (Weiner, H. L., et al., NY Acad. Sci., vol. 778, p. xiii-xviii (1996).

As used herein, the term "cellular immune response element" refers to any molecule that induces a cellular immune response. Preferably, the cellular immune response is a Th2 or Th3 response. Preferably the molecule is a protein, peptide, polypeptide, nucleic acid, oligonucleotide, or polynucleotide. Some cellular immune response elements are well known in the art and include, but are not limited to molecules that can up-regulate or produce polypeptides that decrease autoimmune inflammation, which include but are not limited to polypeptides IL-4 (i.e., GenBank Accession No. M13982; SEQ ID NO:12) and IL-10 (i.e., GenBank Accession No. M57627; SEQ ID NO:14) and nucleic acids encoding IL-4 and IL-10 (i.e., SEQ ID NOs:1 and 3). Cellular immune response elements can also down-regulate or inhibit polypeptides that increase autoimmune inflammation, which include but are not limited to polypeptide TGF-$\beta$ (i.e., GenBank Accession No. M60316; SEQ ID NO:16) and nucleic acids encoding TGF-$\beta$ (i.e., SEQ ID NO: 5). However, it is understood that other cellular immune response elements include those known in the art and those not yet identified. Preferably a cellular immune response element polypeptide or fragment thereof, has an amino acid sequence that is homologous to an amino acid sequence of a cellular immune response element as provided herein, i.e., SEQ ID NOs:12-22. In certain preferred embodiments, a fragment of a cellular immune response element has at least 25 amino acids, more preferably at least 50 amino acids, more preferably at least 150 amino acids, more preferably at least 200 amino acids, more preferably at least 250 amino acids, more preferably at least 300 amino acids, more preferably at least 400 amino acids, more preferably at least 500 amino acids, more preferably at least 600 amino acids, more preferably at least 700 amino acids, more preferably at least 800 amino acids that are homologous to a cellular immune response element as provided herein, i.e., SEQ ID NOs:12-22. The term "homologous" as it refers herein to an amino acid sequence means that the amino acid is at least 70%, more preferably 75%, more preferably 80%, more preferably 85%, more preferably 90%, more preferably 95%, more preferably 98%, or most preferably 100% identical to a known amino acid sequence (for example SEQ ID NOs:12-22).

As used herein, the term "lipofection reagent" refers to a substance used to incorporate genetic material into a cell by means of liposomes. Examples of lipofection reagents include lipofectin, lipofectamine, cationic lipids and neutral co-lipids.

As used herein, the term "plasmid" refers to a construct made up of genetic material (i.e., nucleic acids). It includes genetic elements arranged such that an inserted coding sequence can be transcribed in eukaryotic cells. While the plasmid may include a sequence from a viral nucleic acid, such viral sequence does not cause the incorporation of the plasmid into a viral particle, and the plasmid is therefore a non-viral vector. Preferably a plasmid is closed circular nucleic acid. Preferably, nucleic acid is DNA or RNA. Preferably, plasmids may be introduced into cells by transformation and can replicate autonomously in the cell.

As used herein, the term "pharmaceutically acceptable" refers to a composition suitable for administration to a human. Those of ordinary skill in the art understand that to be suitable for administration to a human, a composition must meet certain criteria, for example, the composition preferably complies with Good Laboratory Practices (GLPs); preferably the composition complies with Good Manufacturing Practices (GMPs); more preferably the composition complies with government regulations such as those set forth by the United States Food and Drug Administration; preferably the composition complies with 21 U.S.C. §301-392.

The terms "replication origin" or "origin of replication" as used herein refers to a nucleotide sequence at which DNA synthesis for the purpose of replicating the nucleic acid sequence begins. This is generally termed an ORI site. Circular bacteria generally have a single ORI site, whereas there can be many ORI sites on each eukaryotic chromosome. This term includes replicons, which as used herein refers to a genetic element that behaves as an autonomous unit during DNA replication. In bacteria, the chromosome functions as a single replicon, whereas eukaryotic chromosomes contain hundreds of replicons in series.

The term "transcription unit" or "expression cassette" refers to a nucleotide sequence which contains at least one coding sequence along with sequence elements which direct the initiation and termination of transcription. A transcription unit may however include additional sequences, which may include sequences involved in post-transcriptional or post-translational processes.

As used herein, the term "transcriptional control sequence" refers to a sequence which controls the rate of transcription of a transcriptionally linked coding region. The term can include elements such as promoters, operators, and enhancers. Preferably, the transcriptional control sequences will include at least one promoter sequence.

As used herein, the term "transcriptionally linked" refers to a system suitable for transcription, transcription will initiate under the direction of a control sequence and proceed through sequences which are transcriptionally linked with that control sequence. Preferably, no mutation is created in the resulting transcript which would alter the resulting translation product. For example, "transcriptionally linked" generally means that the DNA sequences being linked are contiguous, and, in the case of a secretory leader, contiguous and in reading phase. However enhancers do not have to be contiguous. Linking is accomplished by ligation at convenient restriction sites. If such sites do not exist, synthetic oligonucleotide adapters or linkers can be used in accordance with conventional practice.

As used herein, the term "5' untranslated region" or "5' UTR" refers to a sequence located 3' to promoter region and 5' of the downstream coding region. Thus, such a sequence, while transcribed, is upstream (i.e. 5') of the translation initiation codon and therefore is generally not translated into a portion of the polypeptide product.

As used herein, the term "3' untranslated region poly (A) signal" or "3' UTR poly (A) signal" is a sequence located downstream (i.e., 3') of the region encoding material polypeptide. As with the 5' UTR, this region is generally transcribed but not translated. For expression in eukaryotic cells it is generally preferable to include a sequence which signals the addition of a poly-A tail. As with other synthetic genetic elements a synthetic 3' UTR/poly (A) signal has a sequence which differs from naturally-occurring, UTR elements.

As used herein, the term "cytomegalovirus promoter/enhancer sequences" refers to sequences from a cytomegalovirus which are functional in eukaryotic cells as a transcriptional promoter and an upstream enhancer sequence. The enhancer sequence allows transcription to occur at a higher frequency from the associated promoter.

Plasmids described herein, may include one or more of the following: a promoter, 5' untranslated region (5' UTR), 3' UTR/poly (A) signal, and introns may be a synthetic sequence. In this context the term "synthetic" refers to the sequence that is not provided directly by the sequence of a naturally occurring genetic element of that type but rather is an artificially created sequence (i.e., created by an individual by molecular biological methods). While one or more portions of such a synthetic sequence may be the same as portions of naturally occurring sequences, the full sequence over the specified genetic element is different from a naturally occurring genetic element of that type. The use of such synthetic genetic elements allows the functional characteristics of that element to be appropriately designed for the desired function.

As used herein, a polynucleotide including a sequence encoding a cellular immune response element polypeptide or fragment thereof refers to a polynucleotide with a nucleotide sequence that encodes a peptide or protein capable of inducing a cellular immune response as defined herein. It is understood that there are many different nucleotide sequences that could encode a single polypeptide sequence based on normal base paring and codon usage relationships. As such, the term refers to any nucleic acid sequence that would encode a cellular immune response element or fragment thereof. In certain preferred embodiments the polynucleotide including a sequence encoding a cellular immune response element polypeptide or fragment thereof includes a nucleotide sequence that encodes a protein homologous to IL-4, IL-5, IL-10, IL-13, or TGF-β or fragments thereof. Preferably a polynucleotide including a sequence encoding a cellular immune response element polypeptide or fragment thereof includes a contiguous segment of at least 50 nucleotides; more preferably at least 100 nucleotides; more preferably at least 300 nucleotides; more preferably at least 600 nucleotides; more preferably at least 1,000 nucleotides; more preferably at least 1,500 nucleotides; more preferably at least 2,000 nucleotides that are homologous to a sequence encoding polypeptides IL-4, IL-5, IL-10, IL-13, or TGF-β (as shown in SEQ ID NOs:1-5. The term "homologous" as it refers herein to a nucleotide sequence means that the nucleotide sequence is at least 70%, more preferably 75%, more preferably 80%, more preferably 85%, more preferably 90%, more preferably 95%, more preferably 98%, or most preferably 100% identical to a known nucleotide sequence (for example sequences encoding for IL-4, IL-5, IL-10, IL-13, and TGF-β as provided in SEQ ID NOs: 1-5). It is understood that a polynucleotide including a sequence encoding a cellular immune response element polypeptide can contain additional nucleotides, other than the nucleotides forming a sequence that encode a cellular immune response element.

As used herein, the term "sample" or "test sample" refers to any liquid or solid material believed to comprise nucleic acids of interest. A test sample may be obtained from any biological source (i.e., a biological sample), such as cells in culture or a tissue sample or synthetically produced including a chemically synthesized template.

As used herein, the term "sequence encoding a cellular immune response gene or fragment thereof" refers to any nucleic acid sequence encoding a cellular immune response element gene or a fragment thereof. A cellular immune response element gene refers to a polynucleotide that encodes an amino acid sequence corresponding to a polypeptide which may affect inflammation. Examples of cellular immune response element genes include, but are not limited to IL-4, IL-5, IL-10, IL-13 and TGF-β. Preferably the cellular immune response element gene as described herein encodes a peptide with an amino acid sequence corresponding to the amino acid sequence of any of the cellular immune response element polypeptides or fragments thereof based on the normal base pairing and translational codon usage relationships. Preferably, the coding sequence encodes the exact, full amino acid sequence of natural cellular immune response element gene.

As used herein, the term "transduced" refers to a cell with a selected nucleic acid translocated into the cell. A cell is "stably transduced" with a selected nucleic acid when the selected nucleic acid is replicated and passed on to progeny cells. A cell is "transformed" with a selected nucleic acid when the selected nucleic acid is integrated into the cell's genome.

As used herein, the terms "treating," "treatment," or "therapy" refer to curative therapy, prophylactic therapy, and preventive therapy. An example of "preventive therapy" or "prophylactic therapy" is the prevention or lessened targeted pathological condition or disorder. Those in need of treatment include those already with the disorder as well as those prone to have the disorder or those in whom the disorder is to be prevented. Administration can be "chronic" administration which refers to administration of the agent(s) in a continuous mode as opposed to an acute mode, so as to maintain the initial therapeutic effect (activity) for an extended period of time. Administration can also be "intermittent" administration which is treatment that is not consecutively done without interruption but, rather, is cyclic in nature. Administration can also be "in combination with" one or more further therapeutic agents includes simultaneous (concurrent) and consecutive administration in any order.

As used herein, the term "up-regulate" refers to the expression of a gene, or level of RNA or equivalent RNA encoding one or more protein subunits, or activity of one or more protein subunits, such as Th2 cytokines, is greater than that observed in the absence of the compositions disclosed herein. For example, the expression of a protein, such as IL-4, can be increased in order to treat, prevent, ameliorate, or modulate a pathological condition caused or exacerbated by an absence or low level of gene expression.

As used herein, the term "inhibit" or "down-regulate" refers to the expression of a gene, or level of RNA or equivalent RNA encoding one or more protein subunits, or activity of one or more protein subunits, such as Th1 cytokines, is reduced below that observed in the absence of the nucleic acid molecules. In one embodiment, inhibition or down-regulation by an enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of a Th1 cytokine with the compositions disclosed herein is greater in the presence of the composition than in its absence.

As used herein, the term "about" means in quantitative terms plus or minus 10% of the indicated value.

Other features and advantages of the invention will be apparent from the following description of the preferred embodiments and from the claims.

DETAILED DESCRIPTION OF THE INVENTION

Figure 1A:
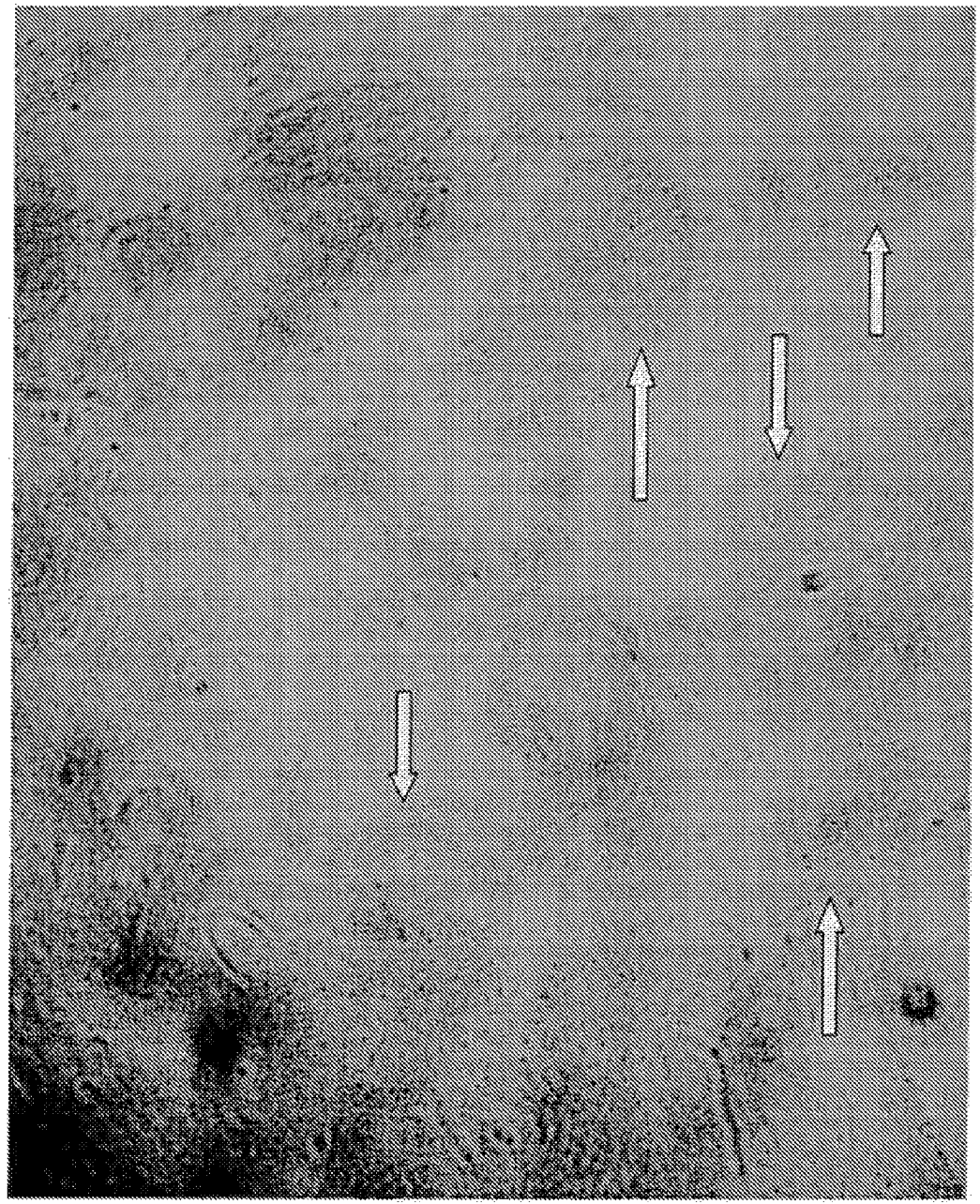
FIG. 1a. Brain histology section processed at nine months of age in vector control (non-treatment group) APP transgenic Alzheimer's disease mouse model after two injections (at six and eight months of age). Arrows in histology section indicate amyloidal plaques labeling after staining with anti amyloidal-β antibody (immunohistochemistry specific staining).
Figure 1B:
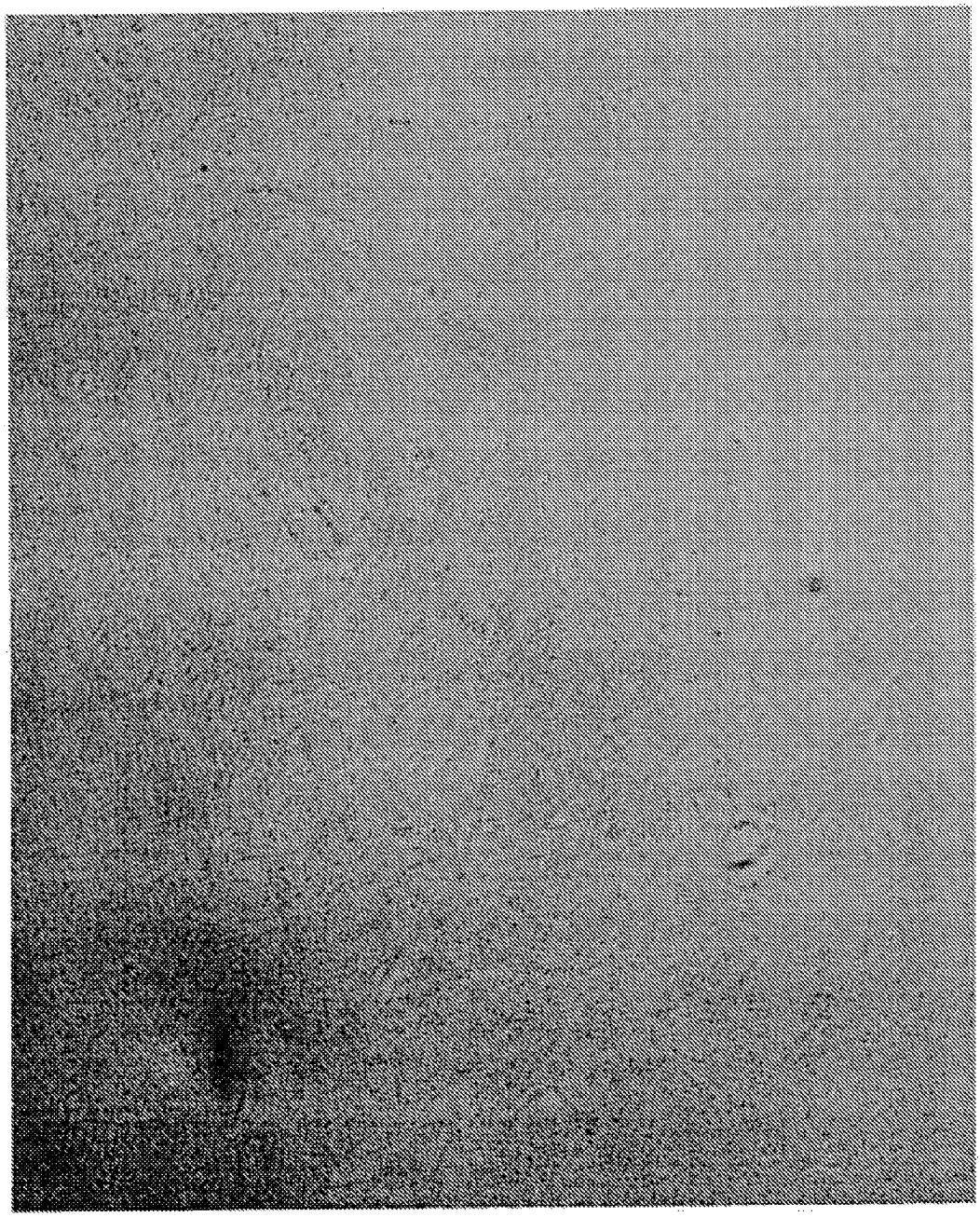
FIG. 1b. Brain histology section processed at nine months of age from an APP transgenic Alzheimer's disease mouse model after two immunizations (at six and eight months of age) with IL-10 gene vaccine. Histology does not indicate any amyloidal plaque labeling after staining with anti amyloidal-β antibody (immunohistochemistry specific staining).
Figure 1C:
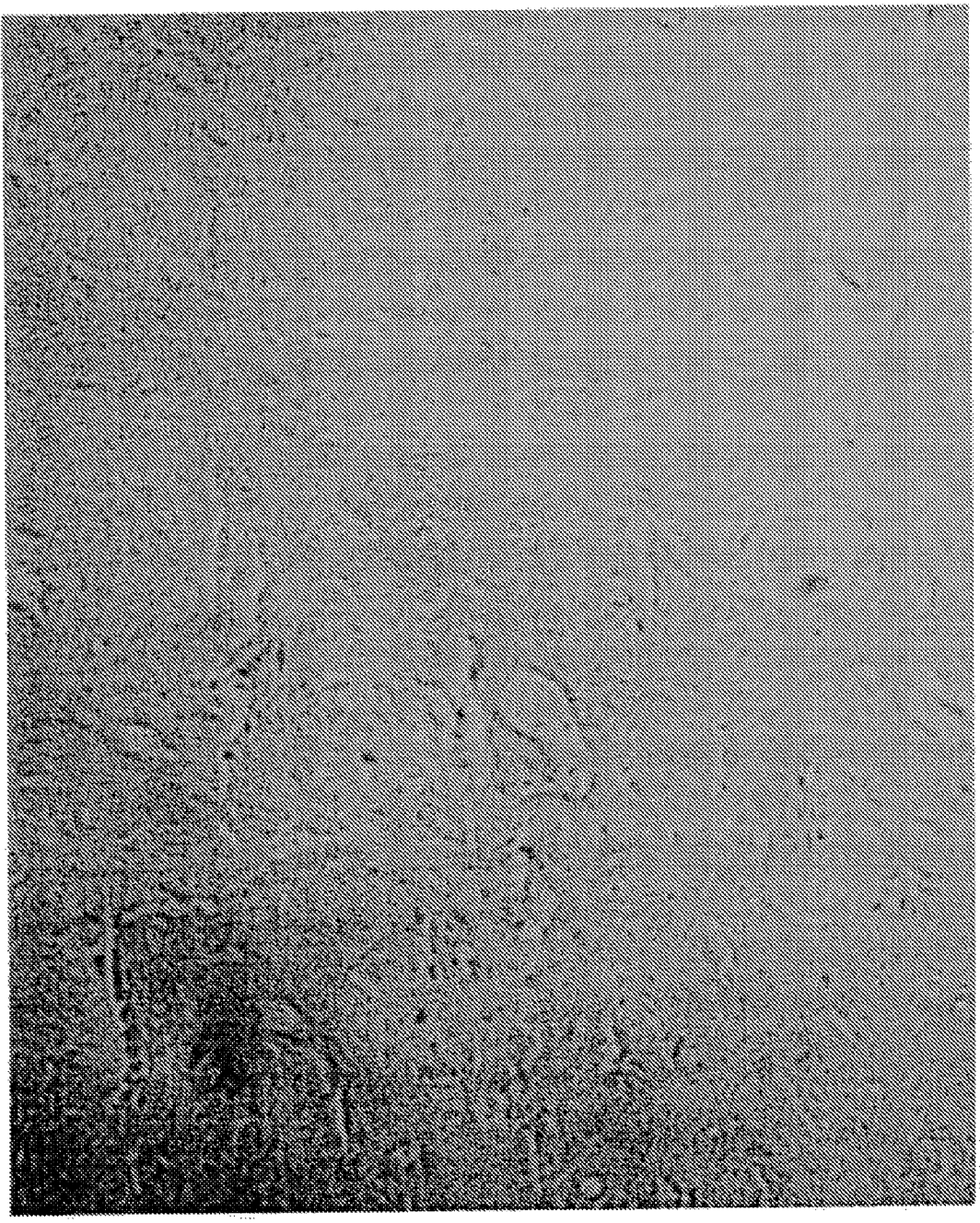
FIG. 1c. Brain histology section processed at nine months of age from an APP transgenic Alzheimer's disease mouse model after two (at six and eight months of age) immunizations with IL-4 gene vaccine. Histology does not indicate any amyloidal plaque labeling after staining with anti amyloidal-β antibody (immunohistochemistry specific staining).
Figure 1D:
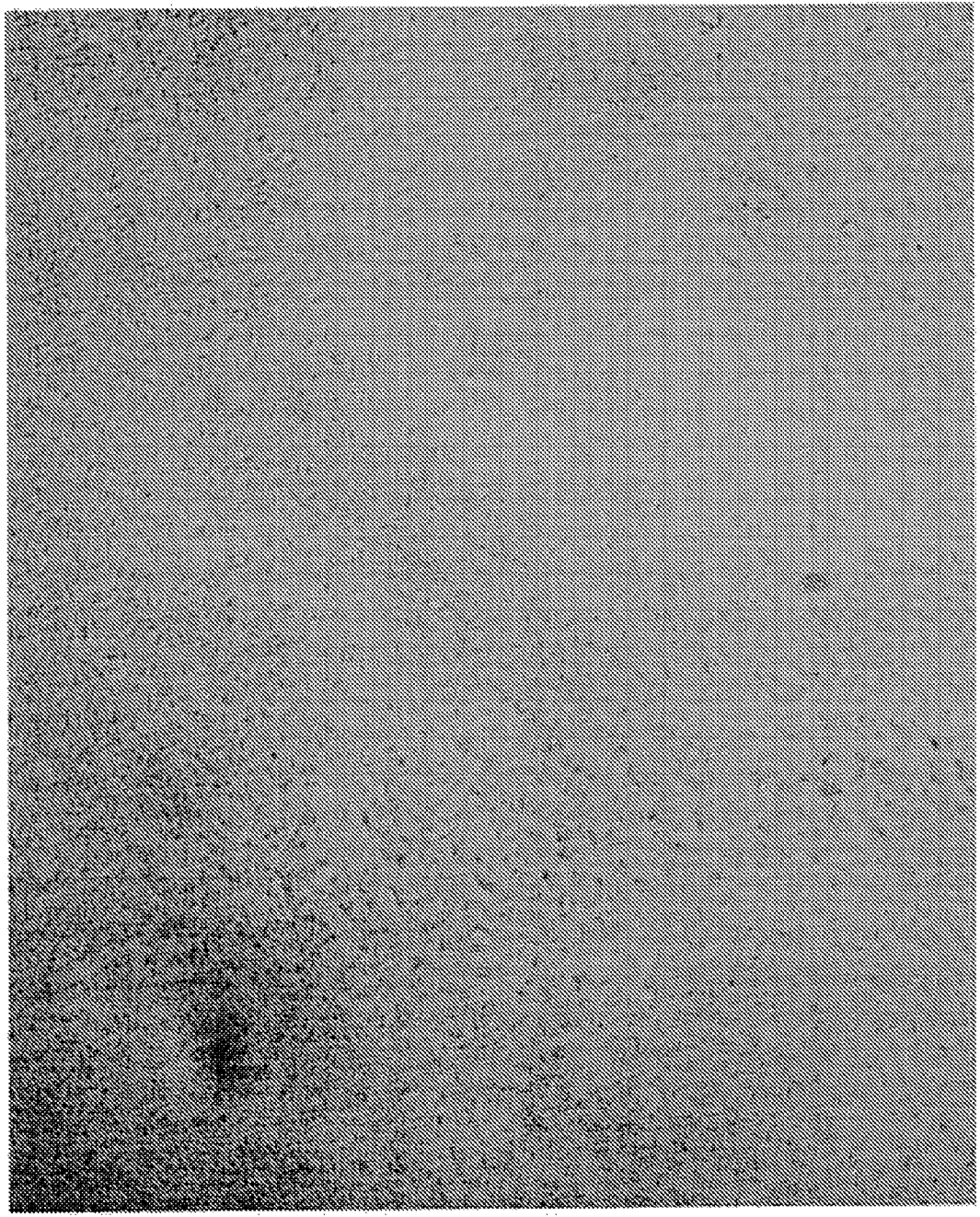
FIG. 1d. Brain histology section processed at nine months of age from an APP transgenic Alzheimer's disease mouse model after two immunizations (at six and eight months of age) with TGF-β gene vaccine. Histology does not indicate any amyloidal plaque labeling after staining with anti amyloidal-β antibody (immunohistochemistry specific staining).

Provided herein include compositions and methods for treatment and/or prevention of neurodegenerative disease such as Alzheimer's disease. In certain aspects, the compositions and methods relate to DNA vaccines and adoptive cellular gene therapies to treat or ameliorate neurodegenerative disease in a subject, preferably a mammal, more preferably a human. In certain aspects, the compositions and methods relate to DNA vaccines encoding a Th2 or Th3 cytokine. The compositions may be prepared and administered in such a manner that a cellular immune response element coding sequence is expressed in the subject to which the composition is administered. These compositions may include expression systems, delivery systems, transfection facilitating materials, and one or more cellular immune response elements.

Allergic diseases have an immune response that deviates toward a T-helper type 2 (Th2) profile and away from the T-helper type 1 (Th1) profile. The Th1 profile is characterized by increased levels molecules that perpetuate an inflammatory response such as IFN-γ and IL-2. The Th2 profile is characterized by increased levels of particular interleukins (IL), such as IL-4, IL-5, IL-10, IL-13, CD4+ T cells and the production of antigen specific IgE. IL-4 is important in IgE synthesis and development of the Th2 response, and IL-5 in eosinophil survival. Immunotherapy results in reversal of this imbalance, with increases in Th1 cytokines, IFN-γ and IL-12, which in turn inhibit the Th2 response. At the same time that genetic vaccination work is burgeoning, so is the work on the low affinity IgG receptor, FCγRIIB, which when occupied, inhibits the IgE-mediated response on mast cells and basophils (Daeron, et al., J Clin. Invest. 95(2): 577-85 (1995)).

In certain embodiments, compositions that reduce inflammation can stimulate expression or produce a gene that decreases inflammation whereas in other embodiments, the composition can affect regulation by inhibiting expression of a gene that increases inflammation such as an antagonist. Double stranded RNA, in particular siRNA can be used for inhibiting expression. RNA can be introduced into a living cell to inhibit gene expression of a target in that cell. The process may be done ex vivo or in vivo. Such RNA compositions and methods of use are further described, for example, in U.S. Pat. No. 6,506,559.

Various approaches may be used to introduce DNA into host cells, including administering naked DNA, DNA complexed with liposomes and various viral vectors. Naked polynucleotide materials, methods, and delivery systems may be used, such as those described in U.S. Pat. Nos. 6,040,295, 5,763,270, and 5,580,859. Polynucleotides are naked in the sense that they are free from any delivery vehicle that can act to facilitate entry into the cell or any material which promotes transfection, such as liposomal formulations, charged lipids such as lipofectin or precipitating agents such as $CaPO_4$.

Vectors for delivering nucleic acids can be viral, non-viral, or physical. See, for example, Rosenberg et al., Science, 242:1575-1578 (1988), and Wolff et al., Proc. Natl. Acad. Sci. USA 86:9011-9014 (1989). Discussion of methods and compositions for use in gene therapy include Eck et al., in Goodman & Gilman's The Pharmacological Basis of Therapeutics, Ninth Edition, Hardman et al., eds., McGray-Hill, New York, (1996), Chapter 5, pp. 77-101; Wilson, Clin. Exp. Immunol. 107 (Suppl. 1):31-32 (1997); Wivel et al., Hematology/Oncology Clinics of North America, Gene Therapy, S. L. Eck, ed., 12(3):483-501 (1998); Romano et al., Stem Cells, 18:19-39 (2000), and the references cited therein. U.S. Pat. No. 6,080,728 also provides a discussion of a wide variety of gene delivery methods and compositions. The routes of delivery include, for example, systemic administration and administration in situ. Well-known viral delivery techniques include the use of adenovirus, retrovirus, lentivirus, foamy virus, herpes simplex virus, and adeno-associated virus vectors.

Viral vectors can also be used for transfection of a mammalian cell and introducing a polynucleotide into a genome. In an indirect method, viral vectors, carrying genetic information, are used to infect target cells removed from the body, and these cells are then re-implanted. Direct in vivo gene transfer into postnatal animals has been reported for formulations of DNA encapsulated in liposomes and DNA encapsulated in proteoliposomes containing viral envelope receptor proteins (Nicolau et al., Proc. Natl. Acad. Sci USA 80:1068-1072 (1983); Kaneda et al., Science 243:375-378 (1989); Mannino et al., Biotechniques 6:682-690 (1988). Viral vectors can be injected or transduced into host cells in vitro, which are then adoptively transferred and serve as delivery vehicles, such as T cells (Nakajima, A., et al., J. Clin. Invest., vol. 17(21), p. 1293-1310 (2001) and Tuohy, V. K., et al., J. Neuroimmunol., vol. 17(2), p. 226-32 (2000)), fibroblasts (Rabinovich, G. A., et al., J. Exp. Med., vol. 19, p. 385-98 (1999)), dendritic cells (DCs) (Kim, S. H., et al., J. Immunol., vol. 166(21), p. 3499-3550 (2001) and Morita, Y., et al., J. Clin. Invest., vol. 17(21), p. 1275-84 (2001)) and stem cells (ATCC or autolougous).

In a certain embodiments the viral vector is preferably a retroviral vector. Retroviral vectors are gene transfer plasmids wherein the heterologous nucleic acid resides between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, which provide a description of methods for efficiently introducing nucleic acids into human cells using such retroviral vectors. Other retroviral vectors include, for example, mouse mammary tumor virus vectors (e.g., Shackleford et al., Proc. Natl. Acad. Sci. U.S.A. 85:9655-9659 (1998)), lentiviruses, and the like. An exemplary viral vector is plentilox-IRES-GFP.

Adoptive Cellular Gene Therapy

The techniques for introducing nucleic acids into cells vary depending upon whether the nucleic acid is transferred into cultured cell in vitro or in vivo in the cells of the intended host. Techniques suitable for the transfer of nucleic acid into mammalian cells in vitro include the use of liposomes, electroporation (Luxembourg A., et al., Expert Opinion Biol. Ther. 7(11):1647-1664 (2007); Kesaraju P, et al., Mol. Ther. 14(3): 416-422 (2006); Luxembourg, et al., Vaccine (24(21):4490-4493 (2006)), microinjection, cell fusion, DEAE-dextran, the calcium phosphate precipitation method, etc. A preferred in vivo gene transfer techniques include transfection with viral (typically, retroviral) vectors and viral coat protein-liposome mediated transfection (Dzau, et al., Trends in Biotechnology 11(5):205-10 (1993)). Suitable vectors can be constructed by any of the methods well known in the art. See, for example, Sambrook et al., Molecular Cloning, A Laboratory Manual, Second Edition, Cold Spring Harbor Press (1989), and Ausubel et al., eds., Current Protocols in Molecular Biology, John Wiley & Sons, N.Y. (1987 and updates). Vectors designed for DNA vaccines are also suitable for delivery of nucleic acid to a mammal, such as pVAX1 (Invitrogen Carlsbad, Calif.). The use of cationic liposomes, such as the CD-Chol/DOPE liposome, has been widely documented as an appropriate vehicle to deliver DNA to a wide range of tissues through intravenous injection of DNA cationic liposome complexes. See Caplen et al., Nature Med., 1:39-46 (1995); Zhu et al., Science, 261:209-211 (1993). Liposome transfer of genes to target cells by fusing with the plasma membrane. Examples of the successful application of liposome complexes include those of Lesson-Wood et al., Human Gene Therapy, 6:395-405 (1995), and Xu et al., Molecular Genetics and Metabolism, 63:103-109 (1998).

Directed delivery of nucleic acid in an individual can be achieved by any of various means known in the art. For example, the nucleic acid source may be combined with an agent that targets cells in damaged tissue, such as an antibody specific for a cell surface membrane protein or the target cell, a ligand for a receptor on the target cells, etc. Where liposomes are employed, proteins which bind to a cell surface membrane protein associated with endocytosis may by used for targeting and/or to facilitate uptake, e.g., capsid proteins or fragments thereof trophic for a particular cell type, antibodies for proteins which undergo internalization in cycling, proteins that target intracellular localization and enhance intracellular half-life. The technique of receptor-mediated endocytosis is described, for example, by Wu, et al., J. Biol. Chem. 262(10):4429-32 (1987); and Wagner, et al., Proc. Natl. Acad. Sci. USA 87(9):3410-4 (1990). For a review of gene marking and gene therapy protocols, see Anderson, Science 256(5058):808-13 (1992).

The methods and compositions provided herein can also be utilized in adoptive cellular gene therapy using genetically engineered immune cells, such as primary T cells, dendritic cells, fibroblasts, and stem cells, that have the ability to migrate to sites of inflammation in organ-specific autoimmune disease to express and deliver immunoregulatory products and/or therapeutic gene products after ex vivo viral transduction. Ex vivo transduction of these cells avoids systemic exposure of the host to the transgene-encoding vector and thus adds to the safety of this approach. Antigen-specific T cell hybridomas were used which expressed anti-inflammatory cytokines such as IL-4, cytokines antagonists such as IL-12 receptor antagonist IL-12p40 or an anti-TNF antibody single chain variable fragment (scFv). All these molecules inhibited disease development and reduced disease severity. CIA models of adoptive cellular gene therapy are examples of convenient gene shuttles for mediating anti-inflammatory gene therapy. Additional studies showed that primary T cells which are more difficult to transducer, are equally effective when expressing IL-12p40, indicating that successful adoptive cellular gene therapy may be applied independent of the cell type used. Therefore, cells such as bone-marrow derived dendritic cells (DCs) can be used to migrate to inflammation sites.

Cells of the dendritic family are especially suited to perform two distinct functions at two discrete locations. In the peripheral tissues, dendritic cells (DC) act as sentinels for "dangerous" antigens. DCs migrate and transport antigens to the lymphoid organ, where they initiate activation of T lymphocytes which are specific for the antigen. During migration, DCs shift from an antigen-capturing mode to a T cell sensitizing mode. DCs also influence the character of T cell differentiation, i.e., the Th1/Th2 balance. DCs provide antigenic and costimulatory signals required for optimal activation of T lymphocytes. DCs and methods of use are further described, for example, in U.S. Pat. No. 6,734,014.

Stem cells may also be used for adoptive cellular gene therapy. Human embryonic stem (ES) cells may be used for the compositions and methods provided herein. ES cells are cultured cell lines derived from inner cell masts of a blastocyst which can be grown indefinitely in an undifferentiated state, yet are also capable of differentiating into all cells of the adult body. Preferably, stem cells appropriate for use in the methods and compositions provided herein are derived from the subject themselves or are engineered in a way to circumvent an immune reaction, such as nuclear transfer or somatic cell nuclear transfer, which entails replacing embryonic stem cell DNA with a subject's DNA. Embryonic stem cells are the most versatile stem cell due to the ability to differentiate into the approximately 200 different cell types found in the adult human body and the only stem cell type for which routine genetic engineering protocols have been developed. Methods of generating stem cells ex vivo are well known in the art and include U.S. Pat. Nos. 6,326,198; 6,261,549; 6,093,531; 5,935,565; 5,670,351; 5,670,147; 5,646,043; 5,437,994.

Vaccination with cDNA requires relatively few injections, and has a quicker build-up phase. The risk of adverse reactions to immunotherapy may also be reduced. Plasmid DNA and its gene expression have been noted to be long lasting (Wolff, et al., Hum. Mol. Genet. 1:363-69 (1992)) and immune responses in primates and rodents have been documented to last for more than one year following DNA vaccination (Donnelly, et al., J Immunol Meth. 176:145-152 (1994); and Raz, et al., Pro. Natl. Acad. Sci. 91:9519-9523 (1994)). It does not appear that plasmid DNA is incorporated into the host genome, but remains as an episome (Tang, et al., Nature. 356:152-4 (1992)). The discovery that naked DNA and RNA is taken up and transiently expressed by muscle cells in vivo has increased interest in using non-viral vehicles for genetic delivery. See Wolff et al., Science, 247, 1465-1468 (1990); Acsadi, et al., Nature, 352, 815-818, (1991). Although naked DNA and RNA can be taken up by mammalian cells, the efficiency of transfection may be increased tremendously if the DNA or RNA is complexed in liposomes (Chen, et al., Gene Therapy 7(19): 1698-705 (2000)).

Administering a polynucleotide to a mammal in vivo, such that a cellular immune response element or fragment thereof is expressed in the mammal, can be achieved using any of many methods known in the art for mammalian gene expression. For example such methods for administering expressible polynucleotides to mammals including expression systems and delivery systems can be found in U.S. Pat. Nos. 6,875,748, 5,763,270, 5,580,859, 6,040,295, and 6,034,072.

Polynucleotide constructs described herein include nucleotide sequences encoding a cellular immune response element or fragment thereof. The polynucleotide is administered such that the polynucleotide is incorporated into cells and expresses a detectable amount of a prophylactically or therapeutically effective amount of a desired cellular immune response element or fragment thereof. Exemplary cellular immune response elements suitable for use as provided herein include IL-4, IL-5, IL-10, IL-13, and TGF-$\beta$.

Expression Systems

Non-viral administration of nucleic acid in vivo has been accomplished by a variety of methods. These include lipofectin liposome fusion: Proc. Natl. Acad. Sci. 84, pp. 7413-7417 (1993); polylysine condensation with and without adenovirus enhancement: Human Gene Therapy 3, pp. 147-154 (1992); and transferrin:transferrin receptor delivery of nucleic acid to cells: Proc. Natl. Acad. Sci. 87, pp. 3410-3414 (1990). The use of a specific composition consisting of polyacrylic acid has been disclosed in WO 94/24983. Naked DNA has been administered as disclosed in WO90/11092.

Thus, in one aspect, a plasmid is provided for expression of a cellular immune response element or fragment thereof which includes an expression cassette, which can also be referred to as a transcription unit. When a plasmid is placed in an environment suitable for gene expression, the transcriptional unit will thus express the polynucleotide including a sequence encoding a cellular immune response element or fragment thereof. The transcription unit includes a transcriptional control sequence, which is transcriptionally linked with a cellular immune response element coding sequence. Transcriptional control sequence may include promoter/enhancer sequences such as cytomegalovirus (CMV) promoter/enhancer sequences. However, those skilled in the art will recognize that a variety of other promoter sequences suitable for expression in eukaryotic cells are known and can similarly be used in the constructs disclosed herein. The level of expression of the gene product will depend on the associated promoter and the presence and activation of an associated enhancer element. In certain embodiments, a sequence encoding a cellular immune response element gene or fragment thereof can be cloned into an expression plasmid which contains the regulatory elements for transcription, translation, RNA stability and replication (i.e., including a transcriptional control sequence). Such expression plasmids are well known in the art and one of ordinary skill would be capable of designing an appropriate expression construct with a polynucleotide including a sequence encoding a cellular immune response element or fragment thereof in such a manner that the cellular immune response element is expressible. There are numerous examples of suitable expression plasmids into which a polynucleotide including a sequence encoding a cellular immune response element gene or fragment thereof could be cloned such as pCI-neo, pUMVC or pcDNA3.

Large quantities of a bacterial host harboring a plasmid for expression of cellular immune response element or fragment thereof may be fermented and the plasmid may be purified for subsequent use. Current human clinical trials using plasmids utilize this approach. Recombinant DNA Advisory Committee Data Management Report, Human Gene Therapy 6: 535-548 (1994).

The purpose of the plasmid is to generally be used in human gene therapy for the efficient delivery of nucleic acid sequences to and expression of therapeutic genes (i.e., cellular immune response elements) in a cell or tissue of a mammal. In particular, the purpose of the plasmid may be to achieve high copy number, avoid potential causes of plasmid instability and provide a means for plasmid selection. As for expression, the nucleic acid cassette contains the necessary elements for expression of the nucleic acid within the cassette. Expression includes the efficient transcription of an inserted gene, nucleic acid sequence, or nucleic acid cassette with the plasmid. Expression products may be proteins, polypeptides or RNA. The nucleic acid sequence can be contained in a nucleic acid cassette. Expression of the nucleic acid can be continuous or regulated.

As an initial step in the process of ultimately obtaining expression of a product encoded by a nucleic acid, is to effect the uptake of the nucleic acid by cells. Uptake of nucleic acid by cells is dependent on a number of factors, one of which is the length of time during which a nucleic acid is in proximity to a cellular surface. For instance, after intramuscular (i.m.) administration of plasmid DNA in buffer, a marked reduction in gene expression is observed if the muscle is massaged, presumably due to DNA leakage out of the muscle either directly or via lymphatic vessels (Human Gene Therapy 4:151-159; 1993). Accordingly, it may be desirable to formulate nucleic acids with compounds which would retard the rate at which nucleic acids diffuse or are carried away from a site at which cellular uptake of the nucleic acid is desired. Further, these compounds could be suitable for administration to an organism by means such as injection while maintaining or regaining the physical characteristics necessary to increase cellular uptake of nucleic acids.

Pharmaceutical Compositions

The compositions provided herein can be administered as a pharmaceutical composition where the compound is formulated with a pharmaceutically acceptable carrier as is well known in the art. Techniques for formulation and administration of pharmaceutical compositions may be found, for example, in "Remington's Pharmaceutical Sciences," (18th ed., Mack Publishing Co., Easton, Pa., 1990). Accordingly, the compounds may be used in the manufacture of a medicament. Pharmaceutical compositions of the compounds may be formulated as solutions or lyophilized powders for parenteral administration. Such powders may be reconstituted by addition of a suitable diluent or other pharmaceutically acceptable carrier prior to use. Such powders also may be sprayed in dry form. A liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, compositions comprising a polynucleotide including a sequence encoding a cellular immune response element or fragment thereof may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. For aqueous compositions used in vivo, the use of sterile pyrogen-free water is preferred. Such formulations will contain an effective amount of a polynucleotide together with a suitable amount of an aqueous solution in order to prepare pharmaceutically acceptable compositions suitable for administration to a mammal, preferably a human. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion or an aqueous or non-aqueous suspension. For rectal administration, the compounds may be combined with excipients such as cocoa butter, glycerin, gelatin or polyethylene glycols and molded into a suppository.

Administration of pharmaceutically acceptable salts of the polynucleotides described herein is included. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. For a helpful discussion of pharmaceutical salts. S. M. Berge et al., Journal of Pharmaceutical Sciences 66:1-19 (1977).

Also provided herein are pharmaceutical compositions for use in supplying a cellular immune response element polypeptide to a mammal, may include a pharmaceutically effective amount of a polynucleotide including a sequence encoding a cellular immune response element or fragment thereof, a container enclosing the carrier and the polynucleotide in a sterile fashion, and means associated with the container for permitting transfer of the polynucleotide from the container to the interstitial space of a tissue, whereby cells of the tissue can take up and express the polynucleotide. The means for permitting such transfer can include a conventional septum that can be penetrated, e.g., by a needle. Alternatively, when the container is a syringe, the means may be considered to comprise the plunger of the syringe or a needle attached to the syringe. Containers may have at least 1, preferably at least 5 or 10, and more preferably at least 50 or 100 micrograms of polynucleotide, to provide one or more unit dosages. For many applications, the container will have at least 500 micrograms or 1 milligram, and often will contain at least 50 or 100 milligrams of polynucleotide.

Also provided are pharmaceutical compositions which may include a polynucleotide including a sequence encoding a cellular immune response element or fragment thereof, in pharmaceutically acceptable administrable form, in a container, and a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert.

Compositions provided herein can be administered as a pharmaceutical composition where the composition is formulated with a pharmaceutically acceptable carrier as is well known in the art. Techniques for formulation and administration may be found, for example, in "Remington's Pharmaceutical Sciences," (18th ed., Mack Publishing Co., Easton, Pa., 1990). Accordingly, compositions may be used in the manufacture of a medicament. It is understood that a pharmaceutically acceptable carrier, or a pharmaceutical composition, or any substance suitable for administration to a mammal should be manufactured and stored in accordance with standards of local regulations. For example many governments have guidelines or rules that regulate various aspects of the manufacture and handling of compositions which are for administration into mammals and/or humans such as sanitation, process validation, equipment and document traceability, and personnel qualification. Preferably, the compositions provided herein, which include a pharmaceutical composition or a pharmaceutically acceptable carrier, are suitable for administration to a human and complies with local regulations, guidelines and/or GMPs (Good Manufacturing Practices) regulations such as those set forth by the United States Food and Drug Administration for such a purpose.

Polynucleotides including a sequence encoding a cellular immune response element or fragment thereof for injection, a preferred route of delivery, may be prepared in unit dosage form in ampules, or in multidose containers. The polynucleotides may be present in such forms as suspensions, solutions, or emulsions in oily or preferably aqueous vehicles. Alternatively, the polynucleotide in a salt form may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The container in which the polynucleotide including a sequence encoding a cellular immune response element or fragment thereof may include a package that is labeled, and the label may bear a notice in the form prescribed by a governmental agency, for example the Food and Drug Administration, which notice is reflective of approval by the agency under Federal law, of the manufacture, use, or sale of the polynucleotide material therein for human administration.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. §301-392. Regulation for biologic material, including products made from the tissues of animals is provided under 42 U.S.C. §262. Similar approval is required by most foreign countries. Regulations vary from country to country, but individual procedures are well known to those in the art and the compositions and methods provided herein preferably comply accordingly.

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tissues or lungs.

As such, provided herein is a pharmaceutical product which may include a polynucleotide including a sequence encoding a cellular immune response element or fragment thereof in solution in a pharmaceutically acceptable injectable carrier and suitable for introduction interstitially into a tissue to cause cells of the tissue to express a cellular immune response element or fragment thereof, a container enclosing the solution, and a notice associated with the container in form prescribed by a governmental agency regulating the manufacture, use, or sale of pharmaceuticals, which notice is reflective of approval by the agency of manufacture, use, or sale of the solution of polynucleotide for human administration.

Administration

In any of the methods disclosed herein, it is preferred that the composition comprising a polynucleotide including a sequence encoding a cellular immune response element or fragment thereof be delivered to a mammal. More preferably, the mammal is a human. Administration of the compositions according to any of the methods disclosed herein can be accomplished according to any of various methods known in the art. For example, U.S. Pat. No. 5,676,954 discloses injection of genetic material, complexed with cationic lipid carriers, into mice. Also, U.S. Pat. Nos. 5,589,466, 5,693,622, 5,580,859, 5,703,055, and PCT international patent application PCT US94/06069 (WO 94/29469), provide methods for delivering compositions comprising naked DNA or DNA cationic lipid complexes to vertebrates.

In certain embodiments, the compound comprising a polynucleotide including a sequence encoding a cellular immune response element or fragment thereof can be administered parenterally, such as intravascularly, intravenously, intraarterially, intramuscularly, subcutaneously, or the like. The compound can be introduced into muscle, skin, brain, lung, liver or spleen tissue. The compound can also be introduced into the blood. Administration can also be orally, nasally, rectally, transdermally or inhalationally via an aerosol. The composition may also be administered as a bolus, or slowly infused.

The polynucleotide including a sequence encoding a cellular immune response element or fragment thereof may be delivered to the interstitial space of tissues of the animal body, including those of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts.

In vivo, muscle cells are particularly competent in their ability to take up and express polynucleotides. This ability may be due to the singular tissue architecture of muscle, comprising multinucleated cells, sarcoplasmic reticulum, and transverse tubular system. Polynucleotides provided herein may enter the muscle through the transverse tubular system, which contains extra cellular fluid and extends deep into the muscle cell. It is also possible that the polynucleotides enter damaged muscle cells which then recover.

Muscle is also advantageously used as a site for the delivery and expression of polynucleotides in a number of therapeutic applications because animals have a proportionately large muscle mass which is conveniently accessed by direct injection through the skin; for this reason, a comparatively large dose of polynucleotides can be deposited in muscle by multiple injections, and repetitive injections, to extend therapy over long periods of time, are easily performed and can be carried out safely and without special skill or devices.

Tissues other than those of muscle may also be advantageously used as injection sites to produce cellular immune response elements. One such condition is the use of a polynucleotide to provide a polypeptide which to be effective must be present in association with cells of a specific type; for example, the cell surface receptors of liver cells associated with cholesterol homeostasis. (Brown and Goldstein, Science 232:34-47 (1986)). In this application, and in many others, such as those in which an enzyme or hormone is the gene product, may not be necessary to achieve high levels of expression in order to effect a valuable therapeutic result.

In certain embodiments, the polynucleotide including a sequence encoding a cellular immune response element or fragment thereof is introduced into tissues using an injectable carrier alone. The carrier preferably is isotonic, hypotonic, or weakly hypertonic, and has a relatively low ionic strength, such as provided by a sucrose solution. The preparation may further advantageously comprise a source of a cytokine which is incorporated into liposomes in the form of a polypeptide or as a polynucleotide.

Compounds comprising a polynucleotide including a sequence encoding a cellular immune response element or fragment thereof be formulated to include other medically useful drugs or biological agents. The compounds also may be administered in conjunction with the administration of other drugs or biological agents useful for the disease or condition that the compounds described herein are directed (see e.g., U.S. Pat. No. 6,413,955 for active ingredients useful for osteoporosis).

Compounds comprising a polynucleotide including a sequence encoding a cellular immune response element or fragment thereof may also be introduced into tissues or cells by a "gene gun." DNA may be coated onto gold microparticles, and delivered intradermally by a particle bombardment device, or "gene gun" as described in the literature (see, for example, Tang et al. (1992), Nature 356:152-154), where gold microprojectiles are coated with the therapeutic DNA, then bombarded into skin cells.

Compounds comprising a polynucleotide including a sequence encoding a cellular immune response element or fragment thereof may also be introduced by nasal and oral administration. Low doses favor active suppression, whereas higher doses favor clonal anergy/deletion. Oral and/or nasal antigen induces T helper 2 (T 2) T cells, such as IL-4 and IL-10, and T helper 3 (Th3) T cells, such as TGF-β, plus CD4+CD25+ regulatory cells and latency-associated peptide T cells. Thus, induction of oral tolerance can be enhanced by administering IL-4, IL-10, anti-IL-12, TGF-β, cholera toxin B subunit, Flt-3 ligand, and anti-CD40 ligands.

Oral and nasal antigen administration (e.g., mucosal tolerance) suppresses animal models of autoimmune diseases including experimental autoimmune encephalitis, uveitis, thyroiditis, myasthenia, arthritis, and diabetes in the non-obese diabetic (NOD) mouse, plus non-autoimmune diseases such as asthma, atherosclerosis, graft rejection, allergy (such as contact sensitivity to dinitrochlorobenzene (DNCB) and nickel allergy), colitis, stroke, and models of Alzheimer's diseases (McGeer P. et al., 42 Neurology 447-449 (1992); Okuray Y., 103(25) PNAS USA 9619-24 (Epub Jun. 12, 2006); Qu B. et al., 244(1-2) J. Neurol. Sci. 151-158 (2006)). Mucosal tolerance may be advantageous for treatment of neurodegenerative diseases such as Alzheimer's disease due to ease of administration, lack of toxicity, and antigen-specific mechanisms of action.

Mucosal tolerance is an attractive approach for treatment of neurodegenerative diseases because of lack of toxicity, ease of administration over time, and antigen-specific mechanisms of action. The successful application of oral tolerance for the treatment of human diseases will depend on dose, developing immune markers to assess immunologic effects, route (nasal versus oral), formulation, mucosal adjuvants, combination therapy, and early therapy.

As employed herein, the phrase "an effective amount" refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Adjuvants

For delivery of a polynucleotide including a sequence encoding a cellular immune response element or fragment thereof to a mammalian system, it is usually preferable to utilize a delivery system. Such a system can provide multiple benefits, notably providing stabilization to protect the integrity of the DNA, as well as assisting in cellular uptake.

In addition, as illustrated by exemplary delivery systems described herein (i.e., transfection reagents), the non-DNA components of the formulation can contribute to an immune system enhancement or activation. As a result, components of a delivery system can be selected in conjunction with a particular gene product to enhance or minimize an immunostimulatory effect.

Immunostimulatory effects are also described for certain nucleotide sequences. For example, Sato et al., Science 273: 352-354 (1996) describes the effects of vaccination with double stranded DNA having certain CpG containing sequences on the production of interferon-γ, interferon-β, and interleukin-12.

Transfection Reagents

Compositions including a polynucleotide including a sequence encoding a cellular immune response element or fragment thereof as provided herein can also include one or more transfection facilitating materials that facilitate delivery of polynucleotides to the interior of a cell, and/or to a desired location within a cell. Many such transfection facilitating materials are commercially available, for example Lipofectin, Lipofectamine, Lipofectamine 2000, Optifect, SuperFect. Examples of transfection facilitating materials include, but are not limited to lipids, preferably cationic lipids; inorganic materials such as calcium phosphate, and metal (e.g., gold or tungsten) particles (e.g., "powder" type delivery solutions); peptides, including cationic peptides, targeting peptides for selective delivery to certain cells or intracellular organelles such as the nucleus or nucleolus, and amphipathic peptides, i.e., helix forming or pore forming peptides; basic proteins, such as histones; asialoproteins; viral proteins (e.g., Sendai virus coat protein); pore-forming proteins; and polymers, including dendrimers, star-polymers, "homogenous" poly-amino acids (e.g., poly-lysine, poly-arginine), "heterogeneous" poly-amino acids (e.g., mixtures of lysine & glycine), co-polymers, polyvinylpyrrolidinone (PVP), and polyethylene glycol (PEG). Furthermore, such auxiliary agents which facilitate and enhance the entry of a polynucleotide into vertebrate cells in vivo, may also be considered "transfection facilitating materials."

Lipofection facilitated transfection is well known in the art as described, for example, in U.S. Pat. Nos. 6,034,072, 6,040,295 and 6,710,035. Certain embodiments compositions provided herein may include lipids as a transfection facilitating material, including cationic lipids (e.g., DOTMA, DMRIE, DOSPA, DC-Chol, GAP-DLRIE), basic lipids (e.g., steryl amine), neutral lipids (e.g., cholesterol), anionic lipids (e.g., phosphatidyl serine), and zwitterionic lipids (e.g., DOPE, DOPC). Preferably, the cationic lipid is mixed with one or more co-lipids. For purposes of definition, the term "co-lipid" refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of noncovalently bonded macroscopic structures, including, for example, liposomes, multilamellar vesicles, unilamellar vesicles, micelles, and simple films.

Delivery can also be through use of DNA transporters. DNA transporters refers to molecules which bind to DNA vectors and are capable of being taken up by epidermal cells. DNA transporters contain a molecular complex capable of noncovalently binding to DNA and efficiently transporting the DNA through the cell membrane. A DNA transporter system can consist of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. A first element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide.

EXAMPLE 1

DNA Vaccine Animal Model Study

Transgenic mice (Tg-2576) containing the K670N/M671L APP double mutation were used for studying the effects of DNA vaccination and Alzheimer's disease. Mice were maintained in the animal house facility at the University of Tennessee, as per the institutional guidelines for such studies. These studies were approved by the Institutional Animal Care and Use Committee of the University of Tennessee in compliance with the Public Health Service policy on humane care and use of laboratory animals. Results from animal model experimentation provide proof-of-principle of adoptive cellular gene therapy in other organisms, particularly humans.

Between four and five months, brain lesions appear in Tg-2576 mice. After nine to ten months, lesions are fully developed. Vaccination beginning around four months shows preventative effects of treatment against Alzheimer's disease whereas vaccination beginning after five months (i.e., beginning at six months) shows treatment of mice that have already developed Alzheimer's disease.

Four month old mice were treated with DNA vaccines encoding IL-4, IL-10 TGF-β were administered with control vector. 100 μg of vaccine were given to each mouse. Mice were boosted twice at two-month intervals. Both male and female Tg-2576 mice were used and maintained until 60 weeks of age. The mice were then sacrificed and their brains were removed, snap-frozen in liquid nitrogen and stored at −80° C.

EXAMPLE 2

Evaluation of Memory

Spatial learning and memory were assessed using the Morris water maze navigation task (water maze). The mice were trained in a round pool of opaque water to learn the location of a platform in order to escape out of the water. The pool was located in the center of the container having any distinct distal spatial cues. All trials were videotaped with an overhead camera. A water tank (80 cm wide, 80 cm deep) was filled with 23° C. water. A hidden circular platform (15 cm wide) was placed 1 cm below the water surface and served as the escape platform for the animal. The maximum swim time for each trial was 90 seconds followed by a 20 second rest on the platform. Each mouse was trained for five days, with four trials per day. The four starting points were randomized for every day of training. Retention tests (probe trial) were performed in the absence of the platform 30 minutes after the last trial. Each animal was released from the position opposite to the target quadrant and allowed to swim for 60 seconds. Following retraining on day 7, the escape platform was moved to the opposite quadrant, and the reversal training procedure was performed on experimental days 8-10. Retention tests for the reversal training were also conducted 30 minutes after the last acquisition trial. For each test, the latency (length of time it took for a mouse to reach the platform) was registered.

EXAMPLE 3

Water Maze Results for Prevention of Alzheimer's Disease

Water maze results of eight month old mice which were vaccinated beginning at four months of age.

| Group | Mouse Identification Number | Latency |
|---|---|---|
| Normal Untreated Mouse | 1 | 6 seconds |
| Tg-2576 Mouse with Control Vector | 1 | 2 minutes |
| Tg-2576 Mouse with IL-10 Vector | 1 | 15 seconds |
| Tg-2576 Mouse with TGF-β Vector | 1 | 23 seconds |

Water maze results of nine month old mice which were vaccinated beginning at four months of age.

| Group | Mouse Identification Number | Latency |
|---|---|---|
| Normal Untreated Mouse | 1 | 6 seconds |
| Tg-2576 Mouse with Control Vector | 1 | 2 minutes 40 seconds |
|  | 2 | 52 seconds |
| Tg-2576 Mouse with IL-10 Vector | 1 | 8 seconds |
|  | 2 | 7 seconds |
|  | 3 | 15 seconds |
| Tg-2576 Mouse with TGF-β Vector | 1 | 1 minute 20 seconds |
|  | 2 | 1 minute 10 seconds |
| Tg-2576 Mouse with IL-4 Vector | 1 | 10 seconds |

These results indicate that the effects of Alzheimer's disease can be prevented and or greatly decreased with early treatment using DNA vaccines.

EXAMPLE 4

Water Maze Results for Treatment of Alzheimer's Disease

Water maze results of seven and a half, nine and a half and eleven month old mice which were vaccinated at six, eight, ten and twelve months of age.

Experiment 1: Results of Mice at Seven and a Half Months

| Group | Mouse Identification Number | Latency |
|---|---|---|
| Normal Untreated Mouse | 1 | 6 seconds |
| Tg-2576 Mouse with Control Vector | 1 | 2 minutes |
| Tg-2576 Mouse with TGF-β Vector | 1 | 23 seconds |
| Tg-2576 Mouse with IL-10 Vector | 1 | 15 seconds |

Experiment 2: Results of Mice at Nine and a Half Months

| Group | Mouse Identification Number | Latency |
|---|---|---|
| Tg-2576 Mouse with Control Vector | 1 | 2 minutes 24 seconds |
|  | 2 | 52 seconds |
| Tg-2576 Mouse with TGF-β Vector | 1 | 1 minute 12 seconds |
|  | 2 | 1 minute 6 seconds |
| Tg-2576 Mouse with IL-4 Vector | 1 | 10 seconds |
| Tg-2576 Mouse with IL-10 Vector | 1 | 8 seconds |
|  | 2 | 7 seconds |

Experiment 3: Results of Mice at Eleven Months

| Group | Mouse Identification Number | Latency |
|---|---|---|
| Tg-2576 Mouse with Control Vector | 1 | 2 minutes 24 seconds |
| Tg-2576 Mouse with Mixed Genes* | 1 | 13 seconds |
| Tg-2576 Mouse with TGF-β Vector | 1 | 1 minute 18 seconds |
|  | 2 | 6 seconds |

-continued

| Group | Mouse Identification Number | Latency |
|---|---|---|
| Tg-2576 Mouse with IL-4 Vector | 1 | 10 seconds |
| Tg-2576 Mouse with IL-10 Vector | 1 | 2 seconds |
| | 2 | 7 seconds |

*Mixed Genes include BDNF, IL-10, IL-4, ApoE

Since brain lesions form around four to five months of age, these mice have already developed Alzheimer's and these results show that Alzheimer's disease can be treated and its effects reduced or reversed by DNA vaccines encoding a cellular immune response element.

EXAMPLE 5

Brain Histology

After anesthesia with Avertin, mice were perfused through the ear with a solution of warm 0.1M phosphate buffer solution (PBS) followed by a warm buffered 1.5% paraformaldehyde solution for two minutes. This was followed by a second fixative containing cold 4% paraformaldehyde for 25 minutes. The animals were decapitated, the brain and bones were exposed and the entire head was immersed in 10% neutral formaldehyde solution and stored overnight. After rinsing with PBS, the brain was dehydrated with ethanol and embedded in paraffin. Groups of 6 μm thick coronal sections starting from the frontal lobe toward the cerebellum were collected and mounted in serial order using a microtome. All sections were mounted and stained with standard Hematoxylin and Eosin (H&E) and Beta Amyloid Immunohistochemical Staining examined for evidence of lesion or neurodegeneration. All sections were examined with a light microscope (Carl Zeiss Axioskop 2 plus HAL 100 with final enlargement×400). Digital images of sections were obtained using a camera (leica) linked to a computer.

Hematoxylin and Eosin (H&E) Staining Protocol

Place slides containing paraffin sections in a slide holder (glass or metal).

Deparfinnize and rehydrate sections using:
3×3' Xylene (blot excess xylene before using ethanol) (StatLab #8400, laboratory grade, Anapath brand, Lewisville, Tex.)
3×3' 100% ethanol
1×3' 95% ethanol
1×3' 80% ethanol
1×5' deionized water While sections are in water, skim surface of hematoxylin with a Kimwipe to remove oxidized particles. Blot excess water from slide holder before going into hematoxylin.

Hematoxylin staining includes:
1×3' Hematoxylin (Poly Scientific #s212A, Harris hematoxylin with glacial acetic acid, Bayshore, N.Y.)
Rinse with deionized water
1×5' tap water (to allow stain to develop)
Dip 8-12 times (fast) in acid ethanol (to destain)
Rinse 2×1' tap water
Rinse 1×2' deionized water (can leave overnight at this stage)

Blot excess water from slide holder before going into eosin.

Eosin staining and dehydration:
1×30 seconds Eosin (up to 45 seconds from an older batch of eosin) (Poly Scientific #s176, Eosin Phloxine stain, Bayshore, N.Y.)
3×5' 95% ethanol
3×5' 100% ethanol (blot excess ethanol before going into xylene)
2×15' Xylene Can leave slides in xylene overnight to get good clearing of any water Place a drop of Permount (xylene based) (Fisher Scientific #SP15-100, histological mounting medium) on the slide using a glass rod, taking care to leave no bubbles.

Angle coverslip and let fall gently onto the slide. Allow Permount to spread beneath the coverslip, covering all the tissue. Dry overnight in a hood.

Beta Amyloid Immunohistochemical Staining Protocol

Beta amyloid is an extracellular filamentous protein deposit found in the brain. It is the major protein component of amyloid cores and neuritic plaques and is also found as a deposit in neurofibrillary tangles. In humans, Alzheimer's disease is the most common cause of senile dementia and is characterized by abnormal filamentous protein deposits in the brain. Beta amyloid deposits are also detected in Lewy body dementia, Down's syndrome, amyloidosis (Dutch type) and in the Guam Parkinson-Dementia complex. Brain tissue with these diseases in addition to brain tissue with Alzheimer's disease were used as positive controls.

Fixation Step: Formalin-fixed, paraffin embedded sections.

Positive Controls: Brain tissue with Alzheimer's disease, Lewy body dementia, Down's syndrome, amyloidosis (Dutch type) and in the Guam Parkinson-Dementia complex.

Solutions and Reagents:
Primary Antibody:
Mouse Anti-Beta-Amyloid (Clone: 6F/3D)(Novocastra, Cat# NCL-B-Amyloid). Optimal dilution 1:100. Species Reactivity: Human, mouse (refer to antibody datasheet for more information).
Secondary Antibody:
Horse Anti-Mouse IgG (H+L), biotinylated (Vector Laboratories, Cat# BA-2000). Optimal dilution 1:500.
Detection Reagent:
HRP-Streptavidin (Vector Laboratories, Cat# SA-5004). Optimal dilution 1:500
Procedure:
1. Paraffin sections to distilled water.
2. Epitope Retrieval: Use Formic Acid Epitope Retrieval Method.
3. Rinse sections in 2 changes of washing buffer, 2 minutes each.
4. Serum Blocking: incubate sections with normal horse serum blocking solution for 30 minutes to block non-specific binding of immunoglobulin.
5. Primary Antibody: incubate sections with Mouse Anti-Beta-Amyloid (Novocastra, Cat# NCL-B-Amyloid) diluted 1:100 in primary antibody dilution buffer for 1 hour at room temperature,
6. Rinse in washing buffer for 2×2 min.
7. Peroxidase Blocking: incubate sections in peroxidase blocking solution for 10 minutes to block endogenous peroxidase activity.
8. Rinse in washing buffer for 3×2 min.
9. Secondary Antibody: incubate sections with biotinylated Horse Anti-Mouse IgG diluted in secondary antibody dilution buffer for 30 minutes at room temperature.

10. Rinse in washing buffer for 3×2 min.
11. Detection: incubate sections with HRP-Streptavidin diluted in HRP-strepavidin dilution buffer for 30 minutes at room temperature.
12. Rinse in washing buffer for 3×2 min.
13. Chromogen/Substrate: incubate sections in DAB peroxidase substrate solution for 5-10 minutes.
14. Rinse in distilled water briefly.
15. Counterstain with Gill's hematoxylin solution or Mayer's hematoxylin solution if desired.
16. Rinse in running tap water for 5 minutes.
17. Dehydrate through 95% ethanol for 2 minutes, 100% ethanol for 2×3 min.
18. Clear in xylene for 2×3 min.
19. Coverslip with permanent mounting medium.
Results:
Staining pattern: Positive staining can be observed in senile plaque cores, plaque periphery and diffuse plaques. In some cases of Alzheimer's disease staining can be observed in vessel walls and in extracellular neurofibrillary tangles.
Notes:
1. Related Protocols: Tau (Tau-2) (Novocastra)
2. Avidin/Biotin Blocking may be needed to block endogenous biotin activity for certain tissues such as kidney, liver, prostate, colon and gut, which may contain endogenous biotin. For frozen sections, snap frozen fresh tissues in isopentane pro-cooled in liquid nitrogen, embedded in OCT compound in cryomolds. Cut 4-8 um cryosat sections and mount on superfrost plus slides. Store slides at −80° C. until needed. Before staining, air dry slides at room temperature for 30 minutes and fix in ice-cold acetone for 5 minutes. Air dry for another 30 minutes. Then start from step 3 for routine immunostaining.

EXAMPLE 6

Water Maze Results for Prevention of Alzheimer's Disease

Water maze results of sixteen month old mice which were vaccinated at six, eight, ten, twelve, and fourteen months of age.

| Group | Mouse Identification Number | Latency |
|---|---|---|
| Normal Untreated Mouse | 1 | 6 seconds |
| Tg-2576 Mouse with Control Vector | 1 | 1 minute 2 seconds |
| Tg-2576 Mouse with IL-10 Vector | 1 | 3 seconds |
|  | 2 | 4 seconds |
| Tg-2576 Mouse with TGF-β Vector | 1 | 14 seconds |
| Tg-2576 Mouse with IL-4 Vector | 1 | 4 seconds |
| Tg-2576 Mouse with IL-10 and IL-4 Vector | 1 | 3 seconds |

Water maze results of thirteen month old mice which were vaccinated at six, eight, ten and twelve months of age.

| Group | Mouse Identification Number | Latency |
|---|---|---|
| Normal Untreated Mouse | 1 | 6 seconds |
| Tg-2576 Mouse with Control | 1 | 3 minutes 40 seconds |
| Vector | 2 | 1 minute 40 seconds |
| Tg-2576 Mouse with IL-10 | 1 | 1 second |
| Vector | 2 | 1 second |
|  | 3 | 8 seconds |
| Tg-2576 Mouse with TGF-β | 1 | 1 minute 20 seconds |
| Vector | 2 | 30 seconds |
| Tg-2576 Mouse with IL-4 Vector | 1 | 10 seconds |
| Tg-2576 Mouse with IL-10 and IL-4 Vector | 1 | 1 second |
|  | 2 | 2 seconds |
| Tg-2576 Mouse with IL-10 and GF-β Vector | 1 | 45 seconds |
|  | 2 | 44 seconds |
| Tg-2576 Mouse with β-amyloid Vector | 1 | 48 seconds |
|  | 2 | 2 minutes 35 seconds |
| Tg-2576 Mouse with β-amyloid and APO-E Vector | 1 | 36 seconds |
| Tg-2576 Mouse with β-amyloid and NGF Vector | 1 | 19 seconds |
|  | 2 | 36 seconds |

EXAMPLE 7

Brain Histology of Mixed Gene Vaccination

Figure 2B:
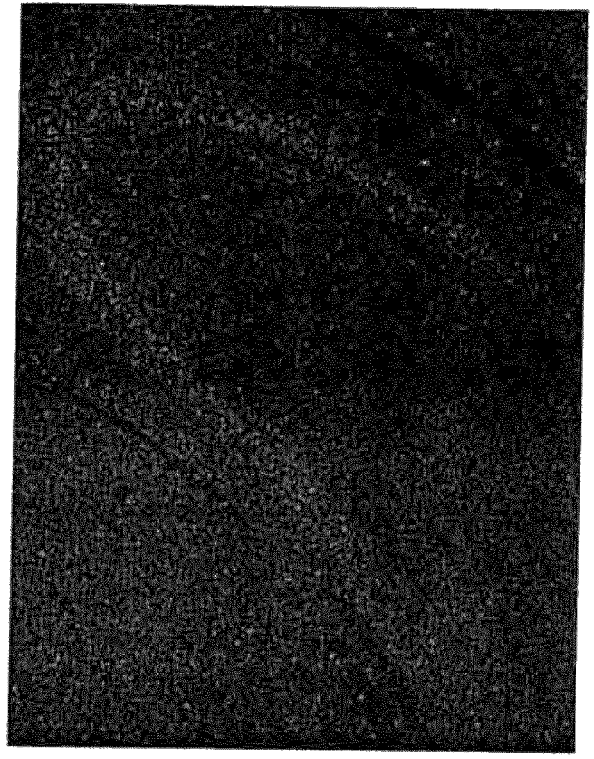
FIGS. 2a and 2b. Brain histology section of hippocampus processed at eighteen months of age from an APP transgenic Alzheimer's disease mouse model after six immunizations (at six, eight, ten, twelve, fourteen and sixteen months of age) with vector only (FIG. 2a) or a mixture of IL-4, IL-10, NGF and Apo-E2 gene vaccines (FIG. 2b). Histology of mixture vaccination does not indicate any amyloidal plaque labeling, consistent with normal, unaffected mice, after staining with anti amyloidal-β antibody (immunohistochemistry specific staining) whereas administration of vector does have labeled amyloidal plaques.
Figure 2A:
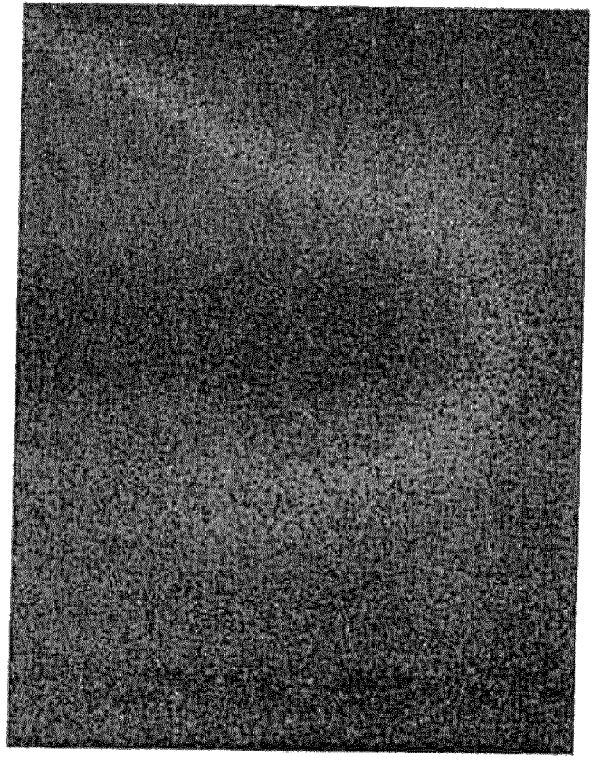

Mice brain tissues of the hippocampus region were processed as described above, from eighteen month old amyloid precursor protein (APP) transgenic mice which received DNA vaccine vector only (FIG. 2a) or a mixture of DNA vaccines containing IL-4, IL-10, Nerve Growth Factor (NGF) and Apo-E2 genes (FIG. 2b). The mice treated were vaccinated at six, eight, ten, twelve, fourteen and sixteen months of age intramuscularly. The dosages of each mixed DNA vaccination treatment were approximately 100 micrograms per injection for each of the four genes (approximately 400 micrograms total). Frozen brain tissues were stained with fluorescent labeled anti-amyloid protein antibody. There is a large amount of amyloid tissues in the untreated mouse brain (FIG. 2a) and markedly decreased amyloid proteins in the mixed DNA vaccine treated mouse brain (FIG. 2b).

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

That which is claimed is:

1. A method of treating or ameliorating Alzheimer's disease in a mammal, consisting essentially of administering to said mammal in vivo, by intramuscular injection, a composition consisting essentially of one or more nucleic acids that induce a cellular immune response; wherein said one or more nucleic acids encode one or more cytokines selected from the group consisting of interleukin-4 (IL-4), interleukin-10 (IL-10), and transforming growth factor-β (TGF-β), and wherein said one or more nucleic acids are vectors and each vector comprises a promoter operably linked to a sequence encoding said cytokine.

2. A method of treating or ameliorating Alzheimer's disease in a mammal, consisting essentially of administering to said mammal in vivo, by intramuscular injection, a composition consisting essentially of:
   (i) one or more nucleic acids that induce a cellular immune response, wherein said one or more nucleic acids encode one or more cytokines selected from the group consisting of IL-4, IL-10 and TGF-β; and
   (ii) one or more nucleic acids selected from the group consisting of nucleic acids encoding apolipoprotein E-2 (ApoE-2), nerve growth factor (NGF), and brain-derived neurotrophic factor (BDNF),
   wherein said one or more nucleic acids are vectors and each vector comprises a promoter operably linked to a sequence encoding said cytokine, ApoE-2, NGF, or BDNF.

3. The method of claim 1, wherein said composition consists essentially of two or more nucleic acids encoding two or more cytokines selected from the group consisting of IL-4, IL-10, and TGF-β.

4. The method of claim 1, wherein said mammal is a human.

5. The method of claim 1, wherein said promoter is suitable for expression in eukaryotic cells.

6. The method of claim 1, wherein said vector is selected from the group consisting of pVAXI, pUMCV, pGCy, and pLentilox-IRES-GFP.

7. The method of claim 4, wherein said administration results in the decrease of amyloid plaque accumulation in the brain of said human in comparison to said human before said administration.

8. A method of decreasing the level of amyloid proteins in the brain of a mammal, consisting essentially of administering to said mammal in vivo, by intramuscular injection, a composition consisting essentially of one or more nucleic acids that induce a cellular immune response;

wherein said one or more nucleic acids encode one or more cytokines selected from the group consisting of IL-4, IL-10, and TGF-β, and wherein said one or more nucleic acids are vectors and each vector comprises a promoter operably linked to a sequence encoding said cytokine.

9. A method of treating or ameliorating Alzheimer's disease in a mammal, comprising administering to said mammal in vivo, by intramuscular injection, a composition comprising one or more nucleic acids that induce a cellular immune response, wherein:

(i) said one or more nucleic acids encode one or more cytokines selected from the group consisting of IL-4, IL-10, and TGF-β;

(ii) said one or more nucleic acids are vectors and each vector comprises a promoter operably linked to a sequence encoding said cytokine; and (iii) said composition does not comprise β-amyloid or β-amyloid$_{1-42}$.

10. The method of claim 9, wherein said composition further comprises one or more nucleic acids selected from the group consisting of nucleic acids encoding ApoE-2, nerve growth factor (NGF), and brain-derived neurotrophic factor (BDNF).

* * * * *